United States Patent
Rathinavelu et al.

(10) Patent No.: US 7,939,557 B2
(45) Date of Patent: May 10, 2011

(54) VASCULAR ENDOTHELIAL RECEPTOR SPECIFIC INHIBITORS

(75) Inventors: Appu Rathinavelu, Weston, FL (US);
Nagarajan Pattabiraman, North Potomac, MD (US); Jayalakshmi Sridhar, Riverside, CA (US); Sivanesan Dakshanamurthy, Arlington, VA (US)

(73) Assignee: Nova Southeastern University, Fort Lauderdale, FL (US)

( * ) Notice: Subject to any disclaimer, the term of this patent is extended or adjusted under 35 U.S.C. 154(b) by 122 days.

(21) Appl. No.: 11/737,375

(22) Filed: Apr. 19, 2007

(65) Prior Publication Data

US 2007/0249575 A1   Oct. 25, 2007

Related U.S. Application Data

(60) Provisional application No. 60/793,382, filed on Apr. 20, 2006.

(51) Int. Cl.
*A61K 31/40* (2006.01)
(52) U.S. Cl. ......... 514/414; 514/415; 514/416; 514/417
(58) Field of Classification Search .................. 514/414, 514/415, 416, 417
See application file for complete search history.

(56) References Cited

U.S. PATENT DOCUMENTS

2005/0182061 A1 * 8/2005 Green et al. ............... 514/249

OTHER PUBLICATIONS

J. Sridhar, N. Akula, D. Sivanesan, M. Narasimhan, A. Rathinavelu, N. Pattabiraman. "Identification of novel angiogenesis inhibitors" Bioorg. Med. Chem. Lett. 2005, pp. 4125-4129.*
B.P. Schneider & K.D. Miller. "Angiogenesis of Breast Cancer" J. Clinical Oncology, 2005, 23(8), pp. 1782-1790.*
Calabresi et al. in "Goodman & Gilman's The Pharmacological Basis of Therapeutics", 10th Edition, McGraw Hill, 2001, pp. 1381-1385.*
Johnson et al., British Journal of Cancer, 2001, vol. 84, pp. 1424-1431.*
Voskoglou-Nomikos et al., Clinical Cancer Research, 2003, vol. 9, pp. 4227-4239.*
Suggitt et al., Clinical Cancer Research, 2005, vol. 11, pp. 971-981.*
Gupta et al., Postgraduate Medical Journal, 2005, vol. 81, pp. 236-242.*

* cited by examiner

*Primary Examiner* — James D Anderson
(74) *Attorney, Agent, or Firm* — Venable LLP; Ann S. Hobbs; Michael E. Nelson

(57) ABSTRACT

The present application describes isoindoles and derivatives thereof, or pharmaceutically acceptable salt forms thereof, which are useful inhibitors of VEGFR.

1 Claim, No Drawings

VASCULAR ENDOTHELIAL RECEPTOR SPECIFIC INHIBITORS

CROSS-REFERENCE TO RELATED APPLICATIONS

This application claims the priority benefit of U.S. Provisional Application No. 60/793,382 filed Apr. 20, 2006, now pending, which is incorporated herein by reference.

FIELD OF THE INVENTION

This invention relates generally to substituted isoindoles, which are vascular endothelial growth factor receptor (VEGFR) inhibitors, pharmaceutical compositions containing the same, and methods of using the same as anti-tumor agents for treatment of cancer (e.g., breast, colorectal, lung, and ovarian).

BACKGROUND OF THE INVENTION

Tumor angiogenesis is one of the essential steps that is required for the growth and metastasis of solid tumors in human. Angiogenesis or neovascularization is the process of generating new capillary of blood vessels derived as extensions from an existing vasculature. The cells that are primarily involved in the process of angiogenesis are endothelial cells that proliferate and organize to form new blood vessels. To achieve the new blood vessel formation, endothelial cells must first escape from their stable location by breaking through the basement membrane, and this degradation is associated with migration of endothelial cells out of the vascular channel toward the angiogenic stimulus. During this process, the sub-endothelial basement membrane, a dense meshwork of collagen, glycoproteins, and proteoglycans, is proteolytically disrupted to allow formation of new capillaries. Though it is an integral component of normal processes such as reproduction and wound healing, it is known to play an important role in other pathological processes ranging from tumor growth, metastasis to inflammation, and ocular diseases.

The angiogenesis process is strongly supported by one of an important series of endothelial cell mitogens called VEGF. The vascular endothelial growth factors (VEGF) play a crucial role in neovascularization of solid tumors. The expression of VEGF has been shown to correlate with the density of micro vessels in various tumors and exhibit higher metastatic ability. Several members of the VEGF family (i.e., A, B, C, and D) and several VEGF receptors: VEGF receptor-1 (known also as Flt-1, fms-like tyrosine kinase 1), VEGF receptor-2 known as Flk-1/KDR (fetal liver kinase-1/kinase insert domain containing receptor) and VEGF receptor-3 (known as Flt-4) have been identified. All of them have seven immunoglobulin homology domains in their extracellular part and an intracellular tyrosine kinase signaling domain split by a kinase insert. By binding to one or more of these receptors, VEGF induces angiogenesis as well as permeabilization of blood vessels and thereby plays a central role in the regulation of vasculogenesis. Recently, it has been demonstrated that the extra cellular domain of VEGFR1 has an important role in vasculogenesis and angiogenesis by fixing the ligand-binding domain to the cell membrane and directly regulating the levels of ligands near the cell surface.

Due to the paramount importance of angiogenesis in the control of tumor growth, it was envisioned that the development of anti-angiogenic drugs will potentially lead to novel therapies against all types of cancers. Several approaches have been used in the development of angiogenic dugs to block the function of VEGF receptors. One approach is targeting angiogenesis by treatment with antibodies against either VEGF or its receptors. For example, Genentech has developed an anti-VEGF antibody that has antiangiogenic and antitumorigenic effects in animal models. So far some success has been achieved through this approach in clinical trials of patients with colorectal cancer. Recently, a 17 amino acid cyclic peptide corresponding to amino acids 79-93 of the VEGF receptor was shown to block angiogenesis. Another common approach is to blocking the kinase activities of VEGFRs with ATP mimics that are selective for the inhibition of the tyrosine kinase activity of Flk-1. Sugen's SU5416 [20] and SU 6668, Astra-Zeneca's ZD4190, and Novartis' PTK787/ZK2284 are compounds that belong to this category and some are presently being tested in clinical trials. More recently, novel low molecular weight VEGFR antagonists, 5-{3-[4-(octadecyloxy)phenyl]propionylamino}-2,4'-oxy-dibenzoic acid (VGA1102) and 5-[N-methyl-N-(4-octadecyloxyphenyl)acetyl]amino-2-ethylthiobenzoic acid (VGA 1155) that prevent angiogenesis by binding to both VEGF receptor 1 (fms-like tyrosine kinase-1 expressing NIH3T3-cells) and VEGF receptor 2 (KDR/flk-1; VEGF receptor 2 transfected) cells at μM concentration range have been reported. VGA1102 and VGA1155 (VGA compounds) appear to be a very specific inhibitors for VEGFR-1 (flt-1) and VEGFR-2 (KDR/flk-1). These compounds do not inhibit the binding of other ligands to their receptors, such as EGF, PDGF, IL-8, PAF, IL-1b, IL-2, IL-4, IL-6, MIPs, TNF-a, and insulin.

Therefore, efficacious and specific inhibitors of VEGFR are needed as potentially valuable therapeutic agents for the treatment of cancer. It is thus desirable to discover new VEGFR inhibitors.

SUMMARY OF THE INVENTION

Accordingly, one object of the present invention is to provide novel isoindoles that are useful as VEGFR inhibitors or pharmaceutically acceptable salts thereof.

It is another object of the present invention to provide pharmaceutical compositions comprising a pharmaceutically acceptable carrier and a therapeutically effective amount of at least one of the compounds of the present invention or a pharmaceutically acceptable salt thereof.

It is another object of the present invention to provide a method for treating cancer (e.g., breast, colorectal, lung, and ovarian), comprising: administering to a host in need of such treatment a therapeutically effective amount of at least one of the compounds of the present invention or a pharmaceutically acceptable salt thereof.

It is another object of the present invention to provide novel isoindoles for use in therapy.

It is another object of the present invention to provide the use of novel isoindoles for the manufacture of a medicament for the treatment of cancer.

These and other objects, which will become apparent during the following detailed description, have been achieved by the inventor's discovery that the presently claimed isoindoles, or pharmaceutically acceptable salts thereof, are VEGFR inhibitors.

DETAILED DESCRIPTION OF PREFERRED EMBODIMENTS

Thus, in an embodiment, the present invention provides a novel method of treating cancer, comprising: administering a therapeutically effective amount of a compound of formula I or a stereoisomer or pharmaceutically acceptable salt thereof:

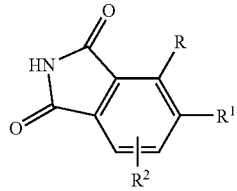

wherein:

one of R and $R^1$ is selected from $NHC(O)R^3$, $NHSO_2R^3$, $CH_2C(O)R^3$, $CH_2SO_2R^3$, $CH_2NHC(O)R^3$, $CH_2NHSO_2R^3$, $CH_2CH_2C(O)R^3$, $CH_2CH_2SO_2R^3$, $NHC(O)CH_2R^3$, $NHSO_2CH_2R^3$, $CH_2C(O)CH_2R^3$, $CH_2SO_2CH_2R^3$, $C(O)NHR^3$, $SO_2NHR^3$, $C(O)CH_2R^3$, $SO_2CH_2R^3$, $CH_2C(O)NHR^3$, $CH_2SO_2NHR^3$, $C(O)NHCH_2R^3$, $SO_2NHCH_2R^3$, $C(O)CH_2CH_2R^3$, and $SO_2CH_2CH_2R^3$, and the other is H;

$R^2$ is selected from H, halogen, $NO_2$, $NH_2$, —CN, $C_{1-2}$ haloalkyl, $C_{1-6}$ alkyl, and $C_{1-6}$ alkoxy;

$R^3$ is selected from phenyl, naphthyl, and a 3-10 membered heteroaryl consisting of carbon atoms and 1-3 heteroatoms selected from oxygen, nitrogen, and $S(O)_p$, wherein $R^3$ is substituted with 0-2 $R^4$;

$R^4$ is independently selected from halogen, $NO_2$, $NH_2$, —CN, $C_{12}$ haloalkyl, $C_{1-6}$ alkyl, $C_{2-6}$ alkenyl, $C_{2-6}$ alkynyl, $C_{1-6}$ alkoxy, CHO, $C(O)C_{1-6}$ alkyl, $C(O)OC_{1-6}$ alkyl, $S(O)_2OC_{1-6}$ alkyl, $C(O)NH_2$, $S(O)_2NH_2$, $S(O)_p$—$R^5$, and $C(O)$—$R^5$;

$R^5$ is selected from $C_{3-8}$ cycloalkyl; $C_{6-10}$ aryl; 3-8 membered heterocycle consisting of carbon atoms and 1-2 heteroatoms selected from oxygen, nitrogen, and $S(O)_p$; and, a 3-10 membered heteroaryl consisting of carbon atoms and 1-3 heteroatoms selected from oxygen, nitrogen, and $S(O)_p$; and, p is independently selected from 0, 1, and 2.

In another embodiment, the present invention provides a novel method of treating cancer, wherein:

one of R and $R^1$ is selected from $NHC(O)R^3$, $NHSO_2R^3$, $CH_2C(O)R^3$, $CH_2SO_2R^3$, $C(O)NHR^3$, $SO_2NHR^3$, $C(O)CH_2R^3$, and $SO_2CH_2R^3$, and the other is H;

$R^2$ is selected from H, halogen, $NO_2$, $NH_2$, —CN, $CF_3$, $C_{1-4}$ alkyl, and $C_{1-4}$ alkoxy;

$R^3$ is selected from phenyl, naphthyl, and a 5-10 membered heteroaryl consisting of carbon atoms and 1-3 heteroatoms selected from oxygen, nitrogen, and $S(O)_p$, wherein $R^3$ is substituted with 0-2 $R^4$;

$R^4$ is independently selected from halogen, $NO_2$, $NH_2$, —CN, $CF_3$, $C_{1-4}$ alkyl, $C_{2-4}$ alkenyl, $C_{2-4}$ alkynyl, $C_{1-4}$ alkoxy, CHO, $C(O)C_{1-4}$ alkyl, $C(O)OC_{1-4}$ alkyl, $S(O)_2OC_{1-4}$ alkyl, $C(O)NH_2$, $S(O)_2NH_2$, $S(O)_p$—$R^5$, and $C(O)$—$R^5$; and, $R^5$ is selected from $C_{3-8}$ cycloalkyl; $C_{6-10}$ aryl; 5-6 membered heterocycle consisting of carbon atoms and 1-2 heteroatoms selected from oxygen, nitrogen, and $S(O)_p$; and, a 5-10 membered heteroaryl consisting of carbon atoms and 1-2 heteroatoms selected from oxygen, nitrogen, and $S(O)_p$.

In another embodiment, the present invention provides a novel method of treating cancer, wherein:

one of R and $R^1$ is selected from $NHC(O)R^3$, $NHSO_2R^3$, $CH_2C(O)R^3$, $CH_2SO_2R^3$, $C(O)NHR^3$, $SO_2NHR^3$, $C(O)CH_2R^3$, and $SO_2CH_2R^3$, and the other is H;

$R^2$ is selected from H, halogen, $NO_2$, $NH_2$, —CN, $CF_3$, $C_{1-4}$ alkyl, and $C_{1-4}$ alkoxy;

$R^3$ is selected from phenyl, naphthyl, and a 5-10 membered heteroaryl consisting of carbon atoms and 1-3 heteroatoms selected from oxygen, nitrogen, and $S(O)_p$, wherein $R^3$ is substituted with 0-2 $R^4$; and, $R^4$ is independently selected from halogen, $NO_2$, $NH_2$, —CN, $CF_3$, $C_{1-4}$ alkyl, $C_{1-4}$ alkoxy, CHO, $C(O)C_{1-4}$ alkyl, $C(O)OC_{1-4}$ alkyl, $S(O)_p$—N-piperdine, $S(O)_p$—N-pyrrolidine, $C(O)$—N-piperdine, and, $C(O)$—N-pyrrolidine.

In another embodiment, the present invention provides a novel method of treating cancer, wherein the compound is selected from:

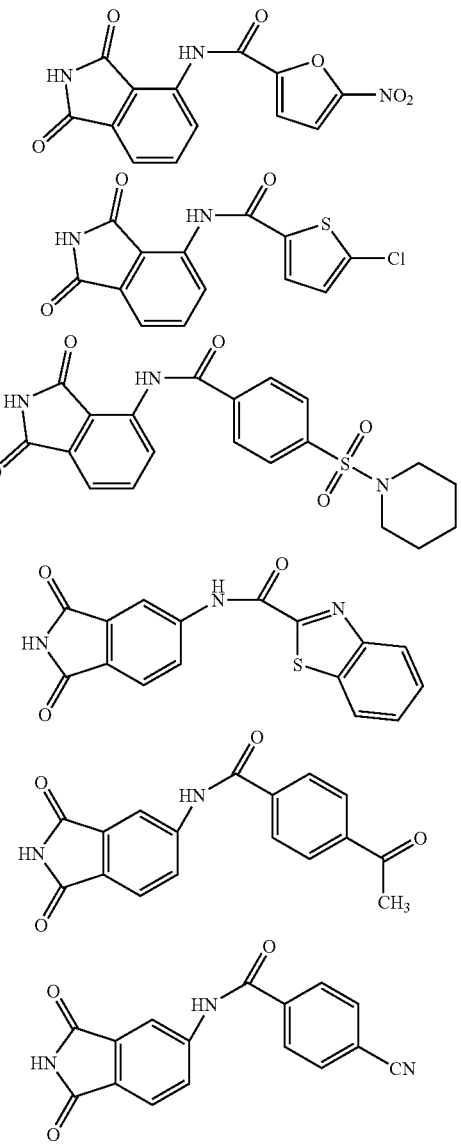

or a pharmaceutically acceptable salt thereof.

In another embodiment, the present invention provides a novel method of treating cancer, wherein the cancer is selected from: breast, colorectal, lung, and ovarian.

In another embodiment, the present invention provides a novel method of treating cancer, comprising: administering a therapeutically effective amount of a compound selected from:

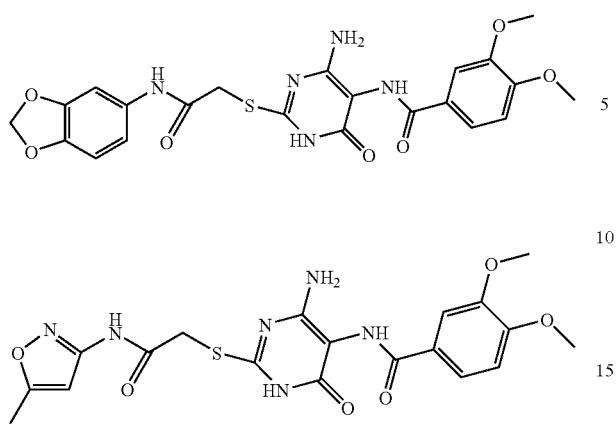

or a pharmaceutically acceptable salt thereof.

In another embodiment, the present invention provides a novel method of treating cancer, wherein the cancer is selected from: breast, colorectal, lung, and ovarian.

In another embodiment, the present invention provides a novel compound of formula I or a stereoisomer or pharmaceutically acceptable salt thereof:

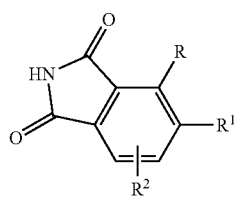

I wherein:

one of R and $R^1$ is selected from $NHC(O)R^3$, $NHSO_2R^3$, $CH_2C(O)R^3$, $CH_2SO_2R^3$, $CH_2NHC(O)R^3$, $CH_2NHSO_2R^3$, $CH_2CH_2C(O)R^3$, $CH_2CH_2SO_2R^3$, $NHC(O)CH_2R^3$, $NHSO_2CH_2R^3$, $CH_2C(O)CH_2R^3$, $CH_2SO_2CH_2R^3$, $C(O)NHR^3$, $SO_2NHR^3$, $C(O)CH_2R^3$, $SO_2CH_2R^3$, $CH_2C(O)NHR^3$, $CH_2SO_2NHR^3$, $C(O)NHCH_2R^3$, $SO_2NHCH_2R^3$, $C(O)CH_2CH_2R^3$, and $SO_2CH_2CH_2R^3$, and the other is H;

$R^2$ is selected from H, halogen, $NO_2$, $NH_2$, —CN, $C_{1-2}$ haloalkyl, $C_{1-6}$ alkyl, and $C_{1-6}$ alkoxy;

$R^3$ is selected from phenyl, naphthyl, and a 3-10 membered heteroaryl consisting of carbon atoms and 1-3 heteroatoms selected from oxygen, nitrogen, and $S(O)_p$, wherein $R^3$ is substituted with 0-2 $R^4$;

$R^4$ is independently selected from halogen, $NO_2$, $NH_2$, —CN, $C_{1-2}$ haloalkyl, $C_{1-6}$ alkyl, $C_{2-6}$ alkenyl, $C_{2-6}$ alkynyl, $C_{1-6}$ alkoxy, CHO, $C(O)C_{1-6}$ alkyl, $C(O)OC_{1-6}$ alkyl, $S(O)_2OC_{1-6}$ alkyl, $C(O)NH_2$, $S(O)_2NH_2$, $S(O)_p$—$R^5$, and $C(O)$—$R^5$;

$R^5$ is selected from $C_{3-8}$ cycloalkyl; $C_{6-10}$ aryl; 3-8 membered heterocycle consisting of carbon atoms and 1-2 heteroatoms selected from oxygen, nitrogen, and $S(O)_p$; and, a 3-10 membered heteroaryl consisting of carbon atoms and 1-3 heteroatoms selected from oxygen, nitrogen, and $S(O)_p$; and, p is independently selected from 0, 1, and 2;

provided that the compound of formula I is other than one of the following compounds:

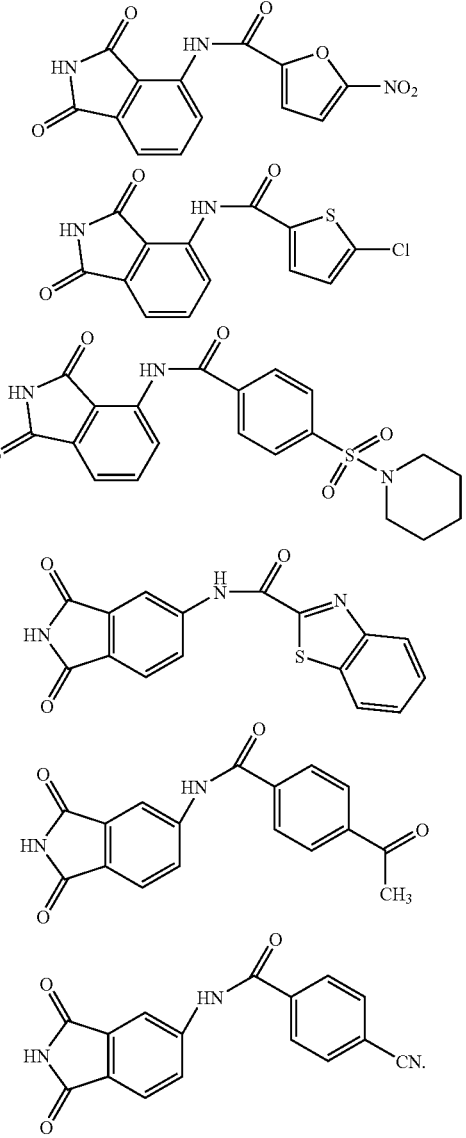

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating cancer (e.g., breast, colorectal, lung, and ovarian), comprising: administering to a patient in need thereof a therapeutically effective amount of a compound of the present invention or a pharmaceutically acceptable salt form thereof.

In another embodiment, the present invention provides a compound of the present invention for use in therapy.

In another embodiment, the present invention provides the use of a compound of the present invention for the manufacture of a medicament for the treatment of cancer.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

All references cited herein are hereby incorporated in their entirety herein by reference.

All examples provided herein are not intended to be limiting, unless stated.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Examples of the molecular weight of compounds of the present invention include those that are (a) less than 500, 550, 600, 650, 700, 750, 800, 850, 900, 950, or 1000 grams per mole, (b) less than 950 grams per mole, (c) less than 850 grams per mole, and, (d) less than 750 grams per mole.

"Substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention includes all isotopes of atoms occurring in the present compounds. Isotopes include those atoms having the same atomic number but different mass numbers. For example isotopes of hydrogen include tritium and deuterium. Isotopes of carbon include C-13 and C-14.

When any variable (e.g., $R^4$) occurs more than one time in any constituent or formula for a compound, its definition at each occurrence is independent of its definition at every other occurrence. Thus, for example, if a group is shown to be substituted with 0-2 $R^4$, then said group may optionally be substituted with up to two $R^4$ groups and $R^4$ at each occurrence is selected independently from the definition of $R^4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with MCPBA and or hydrogen peroxides to afford other compounds of this invention. Thus, all shown amines cover both the shown amine and its N-oxide (N→O) derivative.

"Alkyl" includes both branched and straight-chain saturated aliphatic hydrocarbon groups having the specified number of carbon atoms. $C_{1-6}$ alkyl, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl. "Haloalkyl" includes both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, includes $C_1$, $C_2$, $C_3$, $C_4$, $C_5$, and $C_6$ alkoxy groups. Examples of alkoxy include methoxy, ethoxy, n-propoxy, i-propoxy, n-butoxy, s-butoxy, t-butoxy, n-pentoxy, and s-pentoxy. "Cycloalkyl" includes saturated ring groups, such as cyclopropyl, cyclobutyl, or cyclopentyl. $C_{3-7}$ cycloalkyl includes $C_3$, $C_4$, $C_5$, $C_6$, and $C_7$ cycloalkyl groups. "Alkenyl" includes hydrocarbon chains of either straight or branched configuration and one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups. "Alkynyl" includes hydrocarbon chains of either straight or branched configuration and one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Halo" or "halogen" refers to fluoro, chloro, bromo, and iodo; and "counterion" is used to represent a small, negatively charged species such as chloride, bromide, hydroxide, acetate, and sulfate.

"Carbocycle" means any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

"Heterocycle" means a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen atom can be N, NH, or N-substituent depending on the ring and whether and the location of any substituent. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. When the total number of S and O atoms in the heterocycle exceeds 1, then these heteroatoms are not adjacent to one another. In a typical heterocycle, the total number of S and O atoms in the heterocycle is not more than 1.

"Heteroaryl" means a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. The nitrogen atom can be N, NH, or N-substituent depending on the ring and whether and the location of any substituent. The total number of S and O atoms in the aromatic heterocycle is not more than 1. If the heteroaryl contains more than one ring, only one of the rings need be aromatic.

Examples of heterocycles and heteroaryls include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2, 4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" refers to derivatives of the disclosed compounds wherein the parent compound is modified by making acid or base salts thereof. Examples of pharmaceutically acceptable salts include mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include acetate, formate and benzoate derivatives of alcohol and amine functional groups in the compounds of the present invention.

"Stable compound" and "stable structure" mean a compound that is sufficiently robust to survive isolation to a useful degree of purity from a reaction mixture, and formulation into an efficacious therapeutic agent.

"Substituted" means that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" includes an amount of a compound of the present invention that is effective when administered alone or in combination to inhibit a VEGFR. "Therapeutically effective amount" includes an amount of the combination of compounds claimed that is effective to inhibit a VEGFR. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups in Organic Synthesis*, Wiley and Sons, 1991).

Examples of typical synthetic routes to compounds of the present invention are shown in Schemes 1 and 2 below.

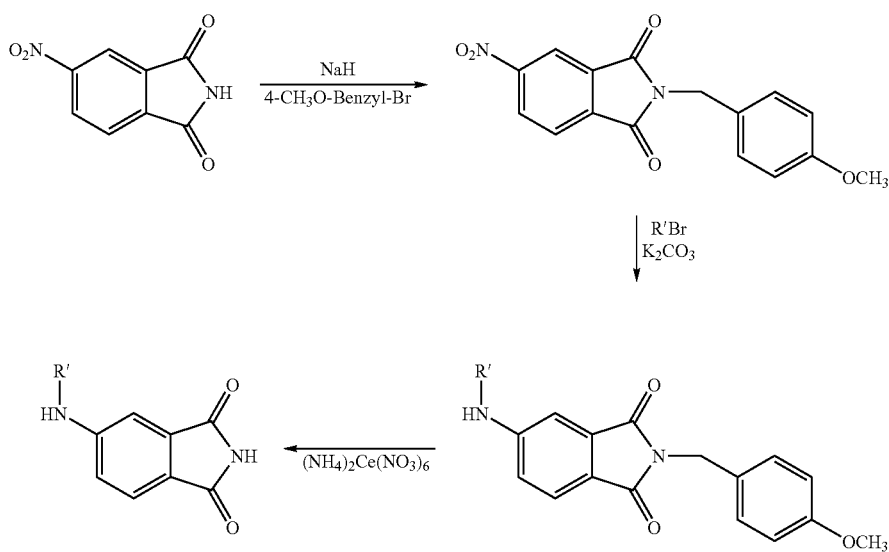

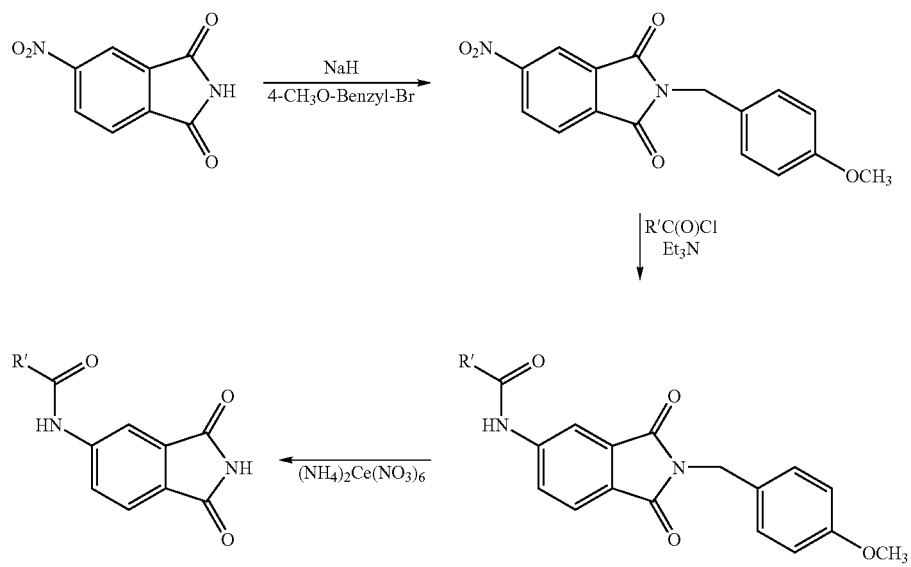

Utility

The compounds of this invention are expected to be useful as antitumor agents anticoagulants for the treatment of cancer (e.g., breast, colorectal, lung, and ovarian).

The effectiveness of some of the compounds of the present invention as inhibitors of a VEGFR was determined in an in vitro angiogenesis assay as well as a VEGF receptor tyrosine kinase assay as described in the Examples.

The compounds of the present invention can be administered alone or in combination with one or more additional therapeutic agents. These include additional compounds of the present invention, other antitumor agents, or other agents that may be beneficially administered with compounds of the present invention.

"Administered in combination" or "combination therapy" means that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the cancer.

Examples of the daily oral dosage of each active ingredient, when used for the indicated effects, can range between (a) 0.001 to 1000 mg/kg of body weight, (b) 0.01 to 100 mg/kg of body weight per day, and (c) 1.0 to 20 mg/kg/day. Intravenously doses can range from 1 to about 10 mg/kg/minute during a constant rate infusion (the dosage can also be calculated using the body's surface area). Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage—forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other antitumor agents, for example, a daily dosage may be about 0.1 to 100 milligrams of the compound of the present invention and about 1 to 7.5 milligrams of the second agent, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Other features of the invention will become apparent in the course of the following descriptions of exemplary embodiments that are given for illustration of the invention and are not intended to be limiting thereof.

EXAMPLES

In Vitro Angiogenesis Assay

Human umbilical vein endothelial cell was purchased from Cambrex Co. (East Rutherford, N.J.) and maintained in EGM (Endothelial Growth Medium) supplemented with 2% FBS, 0.1% EGF, 0.1% Hydrocortisone, 0.1% GA-1000 and 0.4% BBE.

The morphogenesis assay on Matrigel was performed according to the manufacturer's instructions (Chemicon International). The ECMatrix™ kit consists of laminin, collagen type IV, heparan sulfate, proteoglycans, entactin and nidogen. It also contains various growth factors (TGF-β, FGF) and proteolytic enzymes (plasminogen, tPA, MMPs) that are normally produced in EHS tumors. The incubation condition was optimized for maximal tube-formation as follows: 50 μl of EC Matrix™ was suitably diluted in the ratio 9:1 with 10× diluent buffer and used for coating the 96-well plate. The coated plates were incubated at 37° C. for 1 hr. to allow the Matrix solution to solidify. In the meantime the HUVECs that were cultured for 24 hours in EGM with 2% FBS was trypsinised and re-suspended in the growth media and the cells were counted. After 1 hr. pre-incubation of the plate with Matrix solution, the HUVECs were plated at $10^4$ cells/well in the absence or in the presence of different VEGFR inhibitors (1 mM and 10 mM). After 8 hours incubation at 37° C., the cell three-dimensional organization (cellular network structures) was examined under an inverted photomicroscope. Each treatment was performed in triplicate.

Activated endothelial cells form cellular networks (mesh like structures) resembling capillary tubes sprouting into the stromal space. The formation of these cellular networks is a dynamic process, which started migration and alignment of cells followed by the development of capillary tubes like structures, sprouting of new branches and finally the formation of the cellular networks. Although this in vitro angiogenesis kit is designed only as a qualitative assay, we have made an attempt to quantitate the degree of angiogenesis using a scoring method. The scoring was based on the extent of the cellular networks that were observed as follows:

Individual cells, well separated (+++++)
Cells begin to migrate and align themselves (++++)
Cells begin to line but not sprouting (+++)
Visible Sprouting (++)
Closed polygons begins to form (+).

According to our qualitative assessment, the higher the scoring the greater the efficiency of the compound for inhibiting endothelial cell mediated angiogenesis.

Table 1, below, shows the results for Examples 1-8, which are commercially available.

TABLE 1

In Vitro Angiogenesis Assay

| Example # | Structure | Results |
|---|---|---|
| 1 | (structure) | ++++ |

TABLE 1-continued

In Vitro Angiogenesis Assay

| Example # | Structure | Results |
|---|---|---|
| 2 | (isoindoline-1,3-dione)-NH-C(O)-(phenyl)-CN | +++ |
| 3 | (isoindoline-1,3-dione)-NH-C(O)-(phenyl)-C(O)CH₃ | ++ |
| 4 | (isoindoline-1,3-dione)-NH-C(O)-(furan)-NO₂ | +++++ |
| 5 | (isoindoline-1,3-dione)-NH-C(O)-(phenyl)-SO₂-(piperidine) | +++ |
| 6 | (isoindoline-1,3-dione)-NH-C(O)-(thiophene)-Cl | +++ |

The $EC_{50}$ value for anti-antigenic effect of Example 4 was estimated to be 0.025 μM.

Assay of VEGF Receptor Tyrosine Kinase Activity:

Protein Tyrosine Kinases (PTKs) perform a critical role in signal transduction pathways that control cell proliferation, differentiation, metabolism, and apoptosis. Phosphorylation of proteins by PTKs is essential for the regulation of these biological mechanisms and defects in these pathways may result in a number of human diseases, including cancer. The important aspect of these enzymes in cellular regulation is accentuated by the fact that for a large number of kinases a corresponding viral oncogene product has been identified. Protein tyrosine kinase activity is often associated with membrane receptor protein tyrosine kinases (e.g. EGF-, PDGF-, CFS-, IGF-1 and insulin receptor) and soluble non-receptor tyrosine kinases (e.g. p60c-Src, yes, lck, lyn, fyn). Assaying of PTK activity allows for purification and characterization of protein tyrosine kinases, elucidation of their biological functions as well as aiding in development of specific PTK inhibitors. CHEMICON's non-radioactive Tyrosine Kinase Activity Assay provides a simple, convenient and specific method for quantification and comparative determination of a wide range of PTKs. Testing of soluble and receptor tyrosine kinases, in vitro inhibitor screening and the study of PTK regulation can be performed with this assay. Our assay is immunoprecipitation compatible and will not cross-react with serine/threonine kinases.

The non-radioactive Tyrosine Kinase Activity Assay Kit consists of a synthetic Biotinylated Peptide Substrate, a Biotinylated Phosphopeptide, purified Phosphotyrosine specific monoclonal antibody conjugated to horseradish peroxidase (HRP) and other components required to perform 96 ELISA-based assays. The synthetic Biotinylated Substrate, poly [Glu:Tyr], 4:1 contains multiple tyrosine residues and can be phosphorylated by a wide range of PTKs. After quenching the enzyme reaction with an inhibitor, both the phosphorylated and dephosphorylated substrates are immobilized by binding to the streptavidin-coated plate. The fraction of phosphorylated substrate is visualized using a phosphotyrosine monoclonal antibody conjugated to HRP and an ensuing chromagenic substrate reaction. The quantity of phosphate incorporated into the tyrosine kinase substrate is determined utilizing the phosphopeptide standard curve. The assay mixture and start the reaction was be prepared by adding 10 μl of ATP/$MgCl_2$ Solution. The reaction mixture was pre-incubate at 30° C. The reaction time was dependent on the individual tyrosine kinase and was standardized. The enzyme reaction was terminated by adding 10 μl of kinase inhibitor, such as 120 mM EDTA. After termination, 50 μl of reaction mixture was transferred to Streptavidin-coated strip wells and incubated at 37° C. for 30 minutes. The wells were washed four times using IX wash buffer and then 200 μl of blocking buffer solution will be added to each well and incubate at 37° C. for 30 minutes. After removing the blocking buffer 100 μl of diluted mouse anti-Phosphotyrosine HRP conjugate was added to each well and incubated at room temperature for 60 minutes. The wells were washed four times using IX Wash Buffer and then 100 μl of TMB substrate solution were added and the plates are incubate at room temperature for 5-15 minutes. The assay reaction would be terminated by the addition of 100 μl of stop solution and finally, the absorbance was measure on a standard microplate reader at 450 nm.

After testing the anti-antigenic effects of Example 4, the ability of this compound to inhibit the VEGFR linked tyrosine kinase activity was measured. The VEGFR activity was measured by specifically immunoprecipitating the cell lysate using VEGFR antibody (Upstate, Va.) and measuring its activity using the PTK assay. Example 4 was able to inhibit the VEGFR associated tyrosine kinase activity, and the level of inhibition increased as the concentration of the compound increased. The $IC_{50}$ for inhibiting VEGFR kinase was determined to be 0.4 μM.

In addition to inhibiting the angiogenesis under in vitro conditions Example 4 also produced cytotoxicity towards GI-101A and MCF-7, breast carcinoma cell lines.

Representative examples of the present invention include those in the following tables.

TABLE 2

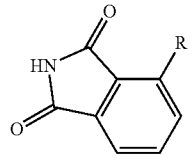

| Ex. # | R | $R^3$ |
|---|---|---|
| 1. | $NHC(O)R^3$ | 5-$NO_2$-furan-2-yl |
| 2. | $NHC(O)R^3$ | 5-$NH_2$-furan-2-yl |
| 3. | $NHC(O)R^3$ | 5-Cl-furan-2-yl |
| 4. | $NHC(O)R^3$ | 5-cyano-furan-2-yl |
| 5. | $NHC(O)R^3$ | 5-$CH_3$-furan-2-yl |
| 6. | $NHC(O)R^3$ | 5-$CF_3$-furan-2-yl |
| 7. | $NHC(O)R^3$ | 5-$CH_3$O-furan-2-yl |
| 8. | $NHC(O)R^3$ | 5-$CH_3$C(O)-furan-2-yl |
| 9. | $NHC(O)R^3$ | 5-$CH_3$OC(O)-furan-2-yl |
| 10. | $NHC(O)R^3$ | 5-$CH_3$OS(O)$_2$-furan-2-yl |
| 11. | $NHC(O)R^3$ | 5-$H_2$NC(O)-furan-2-yl |
| 12. | $NHC(O)R^3$ | 5-$H_2$NS(O)$_2$-furan-2-yl |
| 13. | $NHC(O)R^3$ | 5-N-piperdino-C(O)-furan-2-yl |
| 14. | $NHC(O)R^3$ | 5-N-pyrrolidino-C(O)-furan-2-yl |
| 15. | $NHC(O)R^3$ | 5-N-piperdino-S(O)$_2$-furan-2-yl |
| 16. | $NHC(O)R^3$ | 5-N-pyrrolidino-S(O)$_2$-furan-2-yl |
| 17. | $NHC(O)R^3$ | Furan-2-yl |
| 18. | $NHC(O)R^3$ | 5-$NO_2$-thien-2-yl |
| 19. | $NHC(O)R^3$ | 5-$NH_2$-thien-2-yl |
| 20. | $NHC(O)R^3$ | 5-Cl-thien-2-yl |
| 21. | $NHC(O)R^3$ | 5-cyano-thien-2-yl |
| 22. | $NHC(O)R^3$ | 5-$CH_3$-thien-2-yl |
| 23. | $NHC(O)R^3$ | 5-$CF_3$-thien-2-yl |
| 24. | $NHC(O)R^3$ | 5-$CH_3$O-thien-2-yl |
| 25. | $NHC(O)R^3$ | 5-$CH_3$C(O)-thien-2-yl |
| 26. | $NHC(O)R^3$ | 5-$CH_3$OC(O)-thien-2-yl |
| 27. | $NHC(O)R^3$ | 5-$CH_3$OS(O)$_2$-thien-2-yl |
| 28. | $NHC(O)R^3$ | 5-$H_2$NC(O)-thien-2-yl |
| 29. | $NHC(O)R^3$ | 5-$H_2$NS(O)$_2$-thien-2-yl |
| 30. | $NHC(O)R^3$ | 5-N-piperdino-C(O)-thien-2-yl |
| 31. | $NHC(O)R^3$ | 5-N-pyrrolidino-C(O)-thien-2-yl |
| 32. | $NHC(O)R^3$ | 5-N-piperdino-S(O)$_2$-thien-2-yl |
| 33. | $NHC(O)R^3$ | 5-N-pyrrolidino-S(O)$_2$-thien-2-yl |
| 34. | $NHC(O)R^3$ | Thien-2-yl |
| 35. | $NHC(O)R^3$ | 5-$NO_2$-pyrrol-2-yl |
| 36. | $NHC(O)R^3$ | 5-$NH_2$-pyrrol-2-yl |
| 37. | $NHC(O)R^3$ | 5-Cl-pyrrol-2-yl |
| 38. | $NHC(O)R^3$ | 5-cyano-pyrrol-2-yl |
| 39. | $NHC(O)R^3$ | 5-$CH_3$-pyrrol-2-yl |
| 40. | $NHC(O)R^3$ | 5-$CF_3$-pyrrol-2-yl |
| 41. | $NHC(O)R^3$ | 5-$CH_3$O-pyrrol-2-yl |
| 42. | $NHC(O)R^3$ | 5-$CH_3$C(O)-pyrrol-2-yl |
| 43. | $NHC(O)R^3$ | 5-$CH_3$OC(O)-pyrrol-2-yl |
| 44. | $NHC(O)R^3$ | 5-$CH_3$OS(O)$_2$-pyrrol-2-yl |
| 45. | $NHC(O)R^3$ | 5-$H_2$NC(O)-pyrrol-2-yl |
| 46. | $NHC(O)R^3$ | 5-$H_2$NS(O)$_2$-pyrrol-2-yl |
| 47. | $NHC(O)R^3$ | 5-N-piperdino-C(O)-pyrrol-2-yl |
| 48. | $NHC(O)R^3$ | 5-N-pyrrolidino-C(O)-pyrrol-2-yl |
| 49. | $NHC(O)R^3$ | 5-N-piperdino-S(O)$_2$-pyrrol-2-yl |
| 50. | $NHC(O)R^3$ | 5-N-pyrrolidino-S(O)$_2$-pyrrol-2-yl |
| 51. | $NHC(O)R^3$ | Pyrrol-2-yl |
| 52. | $NHC(O)R^3$ | 4-$NO_2$-phenyl |
| 53. | $NHC(O)R^3$ | 4-$NH_2$-phenyl |
| 54. | $NHC(O)R^3$ | 4-Cl-phenyl |
| 55. | $NHC(O)R^3$ | 4-cyano-phenyl |
| 56. | $NHC(O)R^3$ | 4-$CH_3$-phenyl |
| 57. | $NHC(O)R^3$ | 4-$CF_3$-phenyl |
| 58. | $NHC(O)R^3$ | 4-$CH_3$O-phenyl |
| 59. | $NHC(O)R^3$ | 4-$CH_3$C(O)-phenyl |
| 60. | $NHC(O)R^3$ | 4-$CH_3$OC(O)-phenyl |
| 61. | $NHC(O)R^3$ | 4-$CH_3$OS(O)$_2$-phenyl |
| 62. | $NHC(O)R^3$ | 4-$H_2$NC(O)-phenyl |
| 63. | $NHC(O)R^3$ | 4-$H_2$NS(O)$_2$-phenyl |
| 64. | $NHC(O)R^3$ | 4-N-piperdino-C(O)-phenyl |

TABLE 2-continued

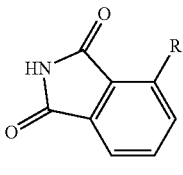

| Ex. # | R | $R^3$ |
|---|---|---|
| 65. | $NHC(O)R^3$ | 4-N-pyrrolidino-C(O)-phenyl |
| 66. | $NHC(O)R^3$ | 4-N-piperdino-S(O)$_2$-phenyl |
| 67. | $NHC(O)R^3$ | 4-N-pyrrolidino-S(O)$_2$-phenyl |
| 68. | $NHC(O)R^3$ | Phen-2-yl |
| 69. | $NHC(O)R^3$ | 5-$NO_2$-benzothiazol-2-yl |
| 70. | $NHC(O)R^3$ | 5-$NH_2$-benzothiazol-2-yl |
| 71. | $NHC(O)R^3$ | 5-Cl-benzothiazol-2-yl |
| 72. | $NHC(O)R^3$ | 5-cyano-benzothiazol-2-yl |
| 73. | $NHC(O)R^3$ | 5-$CH_3$-benzothiazol-2-yl |
| 74. | $NHC(O)R^3$ | 5-$CF_3$-benzothiazol-2-yl |
| 75. | $NHC(O)R^3$ | 5-$CH_3$O-benzothiazol-2-yl |
| 76. | $NHC(O)R^3$ | 5-$CH_3$C(O)-benzothiazol-2-yl |
| 77. | $NHC(O)R^3$ | 5-$CH_3$OC(O)-benzothiazol-2-yl |
| 78. | $NHC(O)R^3$ | 5-$CH_3$OS(O)$_2$-benzothiazol-2-yl |
| 79. | $NHC(O)R^3$ | 5-$H_2$NC(O)-benzothiazol-2-yl |
| 80. | $NHC(O)R^3$ | 5-$H_2$NS(O)$_2$-benzothiazol-2-yl |
| 81. | $NHC(O)R^3$ | 5-N-piperdino-C(O)-benzothiazol-2-yl |
| 82. | $NHC(O)R^3$ | 5-N-pyrrolidino-C(O)-benzothiazol-2-yl |
| 83. | $NHC(O)R^3$ | 5-N-piperdino-S(O)$_2$-benzothiazol-2-yl |
| 84. | $NHC(O)R^3$ | 5-N-pyrrolidino-S(O)$_2$-benzothiazol-2-yl |
| 85. | $NHC(O)R^3$ | Benzothiazol-2-yl |
| 86. | $NHC(O)R^3$ | 5-$NO_2$-benzimidazol-2-yl |
| 87. | $NHC(O)R^3$ | 5-$NH_2$-benzimidazol-2-yl |
| 88. | $NHC(O)R^3$ | 5-Cl-benzimidazol-2-yl |
| 89. | $NHC(O)R^3$ | 5-cyano-benzimidazol-2-yl |
| 90. | $NHC(O)R^3$ | 5-$CH_3$-benzimidazol-2-yl |
| 91. | $NHC(O)R^3$ | 5-$CF_3$-benzimidazol-2-yl |
| 92. | $NHC(O)R^3$ | 5-$CH_3$O-benzimidazol-2-yl |
| 93. | $NHC(O)R^3$ | 5-$CH_3$C(O)-benzimidazol-2-yl |
| 94. | $NHC(O)R^3$ | 5-$CH_3$OC(O)-benzimidazol-2-yl |
| 95. | $NHC(O)R^3$ | 5-$CH_3$OS(O)$_2$-benzimidazol-2-yl |
| 96. | $NHC(O)R^3$ | 5-$H_2$NC(O)-benzimidazol-2-yl |
| 97. | $NHC(O)R^3$ | 5-$H_2$NS(O)$_2$-benzimidazol-2-yl |
| 98. | $NHC(O)R^3$ | 5-N-piperdino-C(O)-benzimidazol-2-yl |
| 99. | $NHC(O)R^3$ | 5-N-pyrrolidino-C(O)-benzimidazol-2-yl |
| 100. | $NHC(O)R^3$ | 5-N-piperdino-S(O)$_2$-benzimidazol-2-yl |
| 101. | $NHC(O)R^3$ | 5-N-pyrrolidino-S(O)$_2$-benzimidazol-2-yl |
| 102. | $NHC(O)R^3$ | Benzimidazol-2-yl |
| 103. | $NHS(O)_2R^3$ | 5-$NO_2$-furan-2-yl |
| 104. | $NHS(O)_2R^3$ | 5-$NH_2$-furan-2-yl |
| 105. | $NHS(O)_2R^3$ | 5-Cl-furan-2-yl |
| 106. | $NHS(O)_2R^3$ | 5-cyano-furan-2-yl |
| 107. | $NHS(O)_2R^3$ | 5-$CH_3$-furan-2-yl |
| 108. | $NHS(O)_2R^3$ | 5-$CF_3$-furan-2-yl |
| 109. | $NHS(O)_2R^3$ | 5-$CH_3$O-furan-2-yl |
| 110. | $NHS(O)_2R^3$ | 5-$CH_3$C(O)-furan-2-yl |
| 111. | $NHS(O)_2R^3$ | 5-$CH_3$OC(O)-furan-2-yl |
| 112. | $NHS(O)_2R^3$ | 5-$CH_3$OS(O)$_2$-furan-2-yl |
| 113. | $NHS(O)_2R^3$ | 5-$H_2$NC(O)-furan-2-yl |
| 114. | $NHS(O)_2R^3$ | 5-$H_2$NS(O)$_2$-furan-2-yl |
| 115. | $NHS(O)_2R^3$ | 5-N-piperdino-C(O)-furan-2-yl |
| 116. | $NHS(O)_2R^3$ | 5-N-pyrrolidino-C(O)-furan-2-yl |
| 117. | $NHS(O)_2R^3$ | 5-N-piperdino-S(O)$_2$-furan-2-yl |
| 118. | $NHS(O)_2R^3$ | 5-N-pyrrolidino-S(O)$_2$-furan-2-yl |
| 119. | $NHS(O)_2R^3$ | Furan-2-yl |
| 120. | $NHS(O)_2R^3$ | 5-$NO_2$-thien-2-yl |
| 121. | $NHS(O)_2R^3$ | 5-$NH_2$-thien-2-yl |
| 122. | $NHS(O)_2R^3$ | 5-Cl-thien-2-yl |
| 123. | $NHS(O)_2R^3$ | 5-cyano-thien-2-yl |
| 124. | $NHS(O)_2R^3$ | 5-$CH_3$-thien-2-yl |
| 125. | $NHS(O)_2R^3$ | 5-$CF_3$-thien-2-yl |
| 126. | $NHS(O)_2R^3$ | 5-$CH_3$O-thien-2-yl |
| 127. | $NHS(O)_2R^3$ | 5-$CH_3$C(O)-thien-2-yl |
| 128. | $NHS(O)_2R^3$ | 5-$CH_3$OC(O)-thien-2-yl |
| 129. | $NHS(O)_2R^3$ | 5-$CH_3$OS(O)$_2$-thien-2-yl |
| 130. | $NHS(O)_2R^3$ | 5-$H_2$NC(O)-thien-2-yl |
| 131. | $NHS(O)_2R^3$ | 5-$H_2$NS(O)$_2$-thien-2-yl |

TABLE 2-continued

[Structure: isoindole-1,3-dione (phthalimide) with R substituent]

| Ex. # | R | R³ |
|---|---|---|
| 132. | NHS(O)₂R³ | 5-N-piperdino-C(O)-thien-2-yl |
| 133. | NHS(O)₂R³ | 5-N-pyrrolidino-C(O)-thien-2-yl |
| 134. | NHS(O)₂R³ | 5-N-piperdino-S(O)₂-thien-2-yl |
| 135. | NHS(O)₂R³ | 5-N-pyrrolidino-S(O)₂-thien-2-yl |
| 136. | NHS(O)₂R³ | Thien-2-yl |
| 137. | NHS(O)₂R³ | 5-NO₂-pyrrol-2-yl |
| 138. | NHS(O)₂R³ | 5-NH₂-pyrrol-2-yl |
| 139. | NHS(O)₂R³ | 5-Cl-pyrrol-2-yl |
| 140. | NHS(O)₂R³ | 5-cyano-pyrrol-2-yl |
| 141. | NHS(O)₂R³ | 5-CH₃-pyrrol-2-yl |
| 142. | NHS(O)₂R³ | 5-CF₃-pyrrol-2-yl |
| 143. | NHS(O)₂R³ | 5-CH₃O-pyrrol-2-yl |
| 144. | NHS(O)₂R³ | 5-CH₃C(O)-pyrrol-2-yl |
| 145. | NHS(O)₂R³ | 5-CH₃OC(O)-pyrrol-2-yl |
| 146. | NHS(O)₂R³ | 5-CH₃OS(O)₂-pyrrol-2-yl |
| 147. | NHS(O)₂R³ | 5-H₂NC(O)-pyrrol-2-yl |
| 148. | NHS(O)₂R³ | 5-H₂NS(O)₂-pyrrol-2-yl |
| 149. | NHS(O)₂R³ | 5-N-piperdino-C(O)-pyrrol-2-yl |
| 150. | NHS(O)₂R³ | 5-N-pyrrolidino-C(O)-pyrrol-2-yl |
| 151. | NHS(O)₂R³ | 5-N-piperdino-S(O)₂-pyrrol-2-yl |
| 152. | NHS(O)₂R³ | 5-N-pyrrolidino-S(O)₂-pyrrol-2-yl |
| 153. | NHS(O)₂R³ | Pyrrol-2-yl |
| 154. | NHS(O)₂R³ | 4-NO₂-phenyl |
| 155. | NHS(O)₂R³ | 4-NH₂-phenyl |
| 156. | NHS(O)₂R³ | 4-Cl-phenyl |
| 157. | NHS(O)₂R³ | 4-cyano-phenyl |
| 158. | NHS(O)₂R³ | 4-CH₃-phenyl |
| 159. | NHS(O)₂R³ | 4-CF₃-phenyl |
| 160. | NHS(O)₂R³ | 4-CH₃O-phenyl |
| 161. | NHS(O)₂R³ | 4-CH₃C(O)-phenyl |
| 162. | NHS(O)₂R³ | 4-CH₃OC(O)-phenyl |
| 163. | NHS(O)₂R³ | 4-CH₃OS(O)₂-phenyl |
| 164. | NHS(O)₂R³ | 4-H₂NC(O)-phenyl |
| 165. | NHS(O)₂R³ | 4-H₂NS(O)₂-phenyl |
| 166. | NHS(O)₂R³ | 4-N-piperdino-C(O)-phenyl |
| 167. | NHS(O)₂R³ | 4-N-pyrrolidino-C(O)-phenyl |
| 168. | NHS(O)₂R³ | 4-N-piperdino-S(O)₂-phenyl |
| 169. | NHS(O)₂R³ | 4-N-pyrrolidino-S(O)₂-phenyl |
| 170. | NHS(O)₂R³ | Phen-2-yl |
| 171. | NHS(O)₂R³ | 5-NO₂-benzothiazol-2-yl |
| 172. | NHS(O)₂R³ | 5-NH₂-benzothiazol-2-yl |
| 173. | NHS(O)₂R³ | 5-Cl-benzothiazol-2-yl |
| 174. | NHS(O)₂R³ | 5-cyano-benzothiazol-2-yl |
| 175. | NHS(O)₂R³ | 5-CH₃-benzothiazol-2-yl |
| 176. | NHS(O)₂R³ | 5-CF₃-benzothiazol-2-yl |
| 177. | NHS(O)₂R³ | 5-CH₃O-benzothiazol-2-yl |
| 178. | NHS(O)₂R³ | 5-CH₃C(O)-benzothiazol-2-yl |
| 179. | NHS(O)₂R³ | 5-CH₃OC(O)-benzothiazol-2-yl |
| 180. | NHS(O)₂R³ | 5-CH₃OS(O)₂-benzothiazol-2-yl |
| 181. | NHS(O)₂R³ | 5-H₂NC(O)-benzothiazol-2-yl |
| 182. | NHS(O)₂R³ | 5-H₂NS(O)₂-benzothiazol-2-yl |
| 183. | NHS(O)₂R³ | 5-N-piperdino-C(O)-benzothiazol-2-yl |
| 184. | NHS(O)₂R³ | 5-N-pyrrolidino-C(O)-benzothiazol-2-yl |
| 185. | NHS(O)₂R³ | 5-N-piperdino-S(O)₂-benzothiazol-2-yl |
| 186. | NHS(O)₂R³ | 5-N-pyrrolidino-S(O)₂-benzothiazol-2-yl |
| 187. | NHS(O)₂R³ | Benzothiazol-2-yl |
| 188. | NHS(O)₂R³ | 5-NO₂-benzimidazol-2-yl |
| 189. | NHS(O)₂R³ | 5-NH₂-benzimidazol-2-yl |
| 190. | NHS(O)₂R³ | 5-Cl-benzimidazol-2-yl |
| 191. | NHS(O)₂R³ | 5-cyano-benzimidazol-2-yl |
| 192. | NHS(O)₂R³ | 5-CH₃-benzimidazol-2-yl |
| 193. | NHS(O)₂R³ | 5-CF₃-benzimidazol-2-yl |
| 194. | NHS(O)₂R³ | 5-CH₃O-benzimidazol-2-yl |
| 195. | NHS(O)₂R³ | 5-CH₃C(O)-benzimidazol-2-yl |
| 196. | NHS(O)₂R³ | 5-CH₃OC(O)-benzimidazol-2-yl |
| 197. | NHS(O)₂R³ | 5-CH₃OS(O)₂-benzimidazol-2-yl |
| 198. | NHS(O)₂R³ | 5-H₂NC(O)-benzimidazol-2-yl |
| 199. | NHS(O)₂R³ | 5-H₂NS(O)₂-benzimidazol-2-yl |
| 200. | NHS(O)₂R³ | 5-N-piperdino-C(O)-benzimidazol-2-yl |
| 201. | NHS(O)₂R³ | 5-N-pyrrolidino-C(O)-benzimidazol-2-yl |
| 202. | NHS(O)₂R³ | 5-N-piperdino-S(O)₂-benzimidazol-2-yl |
| 203. | NHS(O)₂R³ | 5-N-pyrrolidino-S(O)₂-benzimidazol-2-yl |
| 204. | NHS(O)₂R³ | Benzimidazol-2-yl |
| 205. | CH₂C(O)R³ | 5-NO₂-furan-2-yl |
| 206. | CH₂C(O)R³ | 5-NH₂-furan-2-yl |
| 207. | CH₂C(O)R³ | 5-Cl-furan-2-yl |
| 208. | CH₂C(O)R³ | 5-cyano-furan-2-yl |
| 209. | CH₂C(O)R³ | 5-CH₃-furan-2-yl |
| 210. | CH₂C(O)R³ | 5-CF₃-furan-2-yl |
| 211. | CH₂C(O)R³ | 5-CH₃O-furan-2-yl |
| 212. | CH₂C(O)R³ | 5-CH₃C(O)-furan-2-yl |
| 213. | CH₂C(O)R³ | 5-CH₃OC(O)-furan-2-yl |
| 214. | CH₂C(O)R³ | 5-CH₃OS(O)₂-furan-2-yl |
| 215. | CH₂C(O)R³ | 5-H₂NC(O)-furan-2-yl |
| 216. | CH₂C(O)R³ | 5-H₂NS(O)₂-furan-2-yl |
| 217. | CH₂C(O)R³ | 5-N-piperdino-C(O)-furan-2-yl |
| 218. | CH₂C(O)R³ | 5-N-pyrrolidino-C(O)-furan-2-yl |
| 219. | CH₂C(O)R³ | 5-N-piperdino-S(O)₂-furan-2-yl |
| 220. | CH₂C(O)R³ | 5-N-pyrrolidino-S(O)₂-furan-2-yl |
| 221. | CH₂C(O)R³ | Furan-2-yl |
| 222. | CH₂C(O)R³ | 5-NO₂-thien-2-yl |
| 223. | CH₂C(O)R³ | 5-NH₂-thien-2-yl |
| 224. | CH₂C(O)R³ | 5-Cl-thien-2-yl |
| 225. | CH₂C(O)R³ | 5-cyano-thien-2-yl |
| 226. | CH₂C(O)R³ | 5-CH₃-thien-2-yl |
| 227. | CH₂C(O)R³ | 5-CF₃-thien-2-yl |
| 228. | CH₂C(O)R³ | 5-CH₃O-thien-2-yl |
| 229. | CH₂C(O)R³ | 5-CH₃C(O)-thien-2-yl |
| 230. | CH₂C(O)R³ | 5-CH₃OC(O)-thien-2-yl |
| 231. | CH₂C(O)R³ | 5-CH₃OS(O)₂-thien-2-yl |
| 232. | CH₂C(O)R³ | 5-H₂NC(O)-thien-2-yl |
| 233. | CH₂C(O)R³ | 5-H₂NS(O)₂-thien-2-yl |
| 234. | CH₂C(O)R³ | 5-N-piperdino-C(O)-thien-2-yl |
| 235. | CH₂C(O)R³ | 5-N-pyrrolidino-C(O)-thien-2-yl |
| 236. | CH₂C(O)R³ | 5-N-piperdino-S(O)₂-thien-2-yl |
| 237. | CH₂C(O)R³ | 5-N-pyrrolidino-S(O)₂-thien-2-yl |
| 238. | CH₂C(O)R³ | Thien-2-yl |
| 239. | CH₂C(O)R³ | 5-NO₂-pyrrol-2-yl |
| 240. | CH₂C(O)R³ | 5-NH₂-pyrrol-2-yl |
| 241. | CH₂C(O)R³ | 5-Cl-pyrrol-2-yl |
| 242. | CH₂C(O)R³ | 5-cyano-pyrrol-2-yl |
| 243. | CH₂C(O)R³ | 5-CH₃-pyrrol-2-yl |
| 244. | CH₂C(O)R³ | 5-CF₃-pyrrol-2-yl |
| 245. | CH₂C(O)R³ | 5-CH₃O-pyrrol-2-yl |
| 246. | CH₂C(O)R³ | 5-CH₃C(O)-pyrrol-2-yl |
| 247. | CH₂C(O)R³ | 5-CH₃OC(O)-pyrrol-2-yl |
| 248. | CH₂C(O)R³ | 5-CH₃OS(O)₂-pyrrol-2-yl |
| 249. | CH₂C(O)R³ | 5-H₂NC(O)-pyrrol-2-yl |
| 250. | CH₂C(O)R³ | 5-H₂NS(O)₂-pyrrol-2-yl |
| 251. | CH₂C(O)R³ | 5-N-piperdino-C(O)-pyrrol-2-yl |
| 252. | CH₂C(O)R³ | 5-N-pyrrolidino-C(O)-pyrrol-2-yl |
| 253. | CH₂C(O)R³ | 5-N-piperdino-S(O)₂-pyrrol-2-yl |
| 254. | CH₂C(O)R³ | 5-N-pyrrolidino-S(O)₂-pyrrol-2-yl |
| 255. | CH₂C(O)R³ | Pyrrol-2-yl |
| 256. | CH₂C(O)R³ | 4-NO₂-phenyl |
| 257. | CH₂C(O)R³ | 4-NH₂-phenyl |
| 258. | CH₂C(O)R³ | 4-Cl-phenyl |
| 259. | CH₂C(O)R³ | 4-cyano-phenyl |
| 260. | CH₂C(O)R³ | 4-CH₃-phenyl |
| 261. | CH₂C(O)R³ | 4-CF₃-phenyl |
| 262. | CH₂C(O)R³ | 4-CH₃O-phenyl |
| 263. | CH₂C(O)R³ | 4-CH₃C(O)-phenyl |
| 264. | CH₂C(O)R³ | 4-CH₃OC(O)-phenyl |
| 265. | CH₂C(O)R³ | 4-CH₃OS(O)₂-phenyl |

TABLE 2-continued

| Ex. # | R | R³ |
|---|---|---|
| 266. | CH₂C(O)R³ | 4-H₂NC(O)-phenyl |
| 267. | CH₂C(O)R³ | 4-H₂NS(O)₂-phenyl |
| 268. | CH₂C(O)R³ | 4-N-piperdino-C(O)-phenyl |
| 269. | CH₂C(O)R³ | 4-N-pyrrolidino-C(O)-phenyl |
| 270. | CH₂C(O)R³ | 4-N-piperdino-S(O)₂-phenyl |
| 271. | CH₂C(O)R³ | 4-N-pyrrolidino-S(O)₂-phenyl |
| 272. | CH₂C(O)R³ | Phen-2-yl |
| 273. | CH₂C(O)R³ | 5-NO₂-benzothiazol-2-yl |
| 274. | CH₂C(O)R³ | 5-NH₂-benzothiazol-2-yl |
| 275. | CH₂C(O)R³ | 5-Cl-benzothiazol-2-yl |
| 276. | CH₂C(O)R³ | 5-cyano-benzothiazol-2-yl |
| 277. | CH₂C(O)R³ | 5-CH₃-benzothiazol-2-yl |
| 278. | CH₂C(O)R³ | 5-CF₃-benzothiazol-2-yl |
| 279. | CH₂C(O)R³ | 5-CH₃O-benzothiazol-2-yl |
| 280. | CH₂C(O)R³ | 5-CH₃C(O)-benzothiazol-2-yl |
| 281. | CH₂C(O)R³ | 5-CH₃OC(O)-benzothiazol-2-yl |
| 282. | CH₂C(O)R³ | 5-CH₃OS(O)₂-benzothiazol-2-yl |
| 283. | CH₂C(O)R³ | 5-H₂NC(O)-benzothiazol-2-yl |
| 284. | CH₂C(O)R³ | 5-H₂NS(O)₂-benzothiazol-2-yl |
| 285. | CH₂C(O)R³ | 5-N-piperdino-C(O)-benzothiazol-2-yl |
| 286. | CH₂C(O)R³ | 5-N-pyrrolidino-C(O)-benzothiazol-2-yl |
| 287. | CH₂C(O)R³ | 5-N-piperdino-S(O)₂-benzothiazol-2-yl |
| 288. | CH₂C(O)R³ | 5-N-pyrrolidino-S(O)₂-benzothiazol-2-yl |
| 289. | CH₂C(O)R³ | Benzothiazol-2-yl |
| 290. | CH₂C(O)R³ | 5-NO₂-benzimidazol-2-yl |
| 291. | CH₂C(O)R³ | 5-NH₂-benzimidazol-2-yl |
| 292. | CH₂C(O)R³ | 5-Cl-benzimidazol-2-yl |
| 293. | CH₂C(O)R³ | 5-cyano-benzimidazol-2-yl |
| 294. | CH₂C(O)R³ | 5-CH₃-benzimidazol-2-yl |
| 295. | CH₂C(O)R³ | 5-CF₃-benzimidazol-2-yl |
| 296. | CH₂C(O)R³ | 5-CH₃O-benzimidazol-2-yl |
| 297. | CH₂C(O)R³ | 5-CH₃C(O)-benzimidazol-2-yl |
| 298. | CH₂C(O)R³ | 5-CH₃OC(O)-benzimidazol-2-yl |
| 299. | CH₂C(O)R³ | 5-CH₃OS(O)₂-benzimidazol-2-yl |
| 300. | CH₂C(O)R³ | 5-H₂NC(O)-benzimidazol-2-yl |
| 301. | CH₂C(O)R³ | 5-H₂NS(O)₂-benzimidazol-2-yl |
| 302. | CH₂C(O)R³ | 5-N-piperdino-C(O)-benzimidazol-2-yl |
| 303. | CH₂C(O)R³ | 5-N-pyrrolidino-C(O)-benzimidazol-2-yl |
| 304. | CH₂C(O)R³ | 5-N-piperdino-S(O)₂-benzimidazol-2-yl |
| 305. | CH₂C(O)R³ | 5-N-pyrrolidino-S(O)₂-benzimidazol-2-yl |
| 306. | CH₂C(O)R³ | Benzimidazol-2-yl |
| 307. | CH₂S(O)₂R³ | 5-NO₂-furan-2-yl |
| 308. | CH₂S(O)₂R³ | 5-NH₂-furan-2-yl |
| 309. | CH₂S(O)₂R³ | 5-Cl-furan-2-yl |
| 310. | CH₂S(O)₂R³ | 5-cyano-furan-2-yl |
| 311. | CH₂S(O)₂R³ | 5-CH₃-furan-2-yl |
| 312. | CH₂S(O)₂R³ | 5-CF₃-furan-2-yl |
| 313. | CH₂S(O)₂R³ | 5-CH₃O-furan-2-yl |
| 314. | CH₂S(O)₂R³ | 5-CH₃C(O)-furan-2-yl |
| 315. | CH₂S(O)₂R³ | 5-CH₃OC(O)-furan-2-yl |
| 316. | CH₂S(O)₂R³ | 5-CH₃OS(O)₂-furan-2-yl |
| 317. | CH₂S(O)₂R³ | 5-H₂NC(O)-furan-2-yl |
| 318. | CH₂S(O)₂R³ | 5-H₂NS(O)₂-furan-2-yl |
| 319. | CH₂S(O)₂R³ | 5-N-piperdino-C(O)-furan-2-yl |
| 320. | CH₂S(O)₂R³ | 5-N-pyrrolidino-C(O)-furan-2-yl |
| 321. | CH₂S(O)₂R³ | 5-N-piperdino-S(O)₂-furan-2-yl |
| 322. | CH₂S(O)₂R³ | 5-N-pyrrolidino-S(O)₂-furan-2-yl |
| 323. | CH₂S(O)₂R³ | Furan-2-yl |
| 324. | CH₂S(O)₂R³ | 5-NO₂-thien-2-yl |
| 325. | CH₂S(O)₂R³ | 5-NH₂-thien-2-yl |
| 326. | CH₂S(O)₂R³ | 5-Cl-thien-2-yl |
| 327. | CH₂S(O)₂R³ | 5-cyano-thien-2-yl |
| 328. | CH₂S(O)₂R³ | 5-CH₃-thien-2-yl |
| 329. | CH₂S(O)₂R³ | 5-CF₃-thien-2-yl |
| 330. | CH₂S(O)₂R³ | 5-CH₃O-thien-2-yl |
| 331. | CH₂S(O)₂R³ | 5-CH₃C(O)-thien-2-yl |
| 332. | CH₂S(O)₂R³ | 5-CH₃OC(O)-thien-2-yl |
| 333. | CH₂S(O)₂R³ | 5-CH₃OS(O)₂-thien-2-yl |
| 334. | CH₂S(O)₂R³ | 5-H₂NC(O)-thien-2-yl |
| 335. | CH₂S(O)₂R³ | 5-H₂NS(O)₂-thien-2-yl |
| 336. | CH₂S(O)₂R³ | 5-N-piperdino-C(O)-thien-2-yl |
| 337. | CH₂S(O)₂R³ | 5-N-pyrrolidino-C(O)-thien-2-yl |
| 338. | CH₂S(O)₂R³ | 5-N-piperdino-S(O)₂-thien-2-yl |
| 339. | CH₂S(O)₂R³ | 5-N-pyrrolidino-S(O)₂-thien-2-yl |
| 340. | CH₂S(O)₂R³ | Thien-2-yl |
| 341. | CH₂S(O)₂R³ | 5-NO₂-pyrrol-2-yl |
| 342. | CH₂S(O)₂R³ | 5-NH₂-pyrrol-2-yl |
| 343. | CH₂S(O)₂R³ | 5-Cl-pyrrol-2-yl |
| 344. | CH₂S(O)₂R³ | 5-cyano-pyrrol-2-yl |
| 345. | CH₂S(O)₂R³ | 5-CH₃-pyrrol-2-yl |
| 346. | CH₂S(O)₂R³ | 5-CF₃-pyrrol-2-yl |
| 347. | CH₂S(O)₂R³ | 5-CH₃O-pyrrol-2-yl |
| 348. | CH₂S(O)₂R³ | 5-CH₃C(O)-pyrrol-2-yl |
| 349. | CH₂S(O)₂R³ | 5-CH₃OC(O)-pyrrol-2-yl |
| 350. | CH₂S(O)₂R³ | 5-CH₃OS(O)₂-pyrrol-2-yl |
| 351. | CH₂S(O)₂R³ | 5-H₂NC(O)-pyrrol-2-yl |
| 352. | CH₂S(O)₂R³ | 5-H₂NS(O)₂-pyrrol-2-yl |
| 353. | CH₂S(O)₂R³ | 5-N-piperdino-C(O)-pyrrol-2-yl |
| 354. | CH₂S(O)₂R³ | 5-N-pyrrolidino-C(O)-pyrrol-2-yl |
| 355. | CH₂S(O)₂R³ | 5-N-piperdino-S(O)₂-pyrrol-2-yl |
| 356. | CH₂S(O)₂R³ | 5-N-pyrrolidino-S(O)₂-pyrrol-2-yl |
| 357. | CH₂S(O)₂R³ | Pyrrol-2-yl |
| 358. | CH₂S(O)₂R³ | 4-NO₂-phenyl |
| 359. | CH₂S(O)₂R³ | 4-NH₂-phenyl |
| 360. | CH₂S(O)₂R³ | 4-Cl-phenyl |
| 361. | CH₂S(O)₂R³ | 4-cyano-phenyl |
| 362. | CH₂S(O)₂R³ | 4-CH₃-phenyl |
| 363. | CH₂S(O)₂R³ | 4-CF₃-phenyl |
| 364. | CH₂S(O)₂R³ | 4-CH₃O-phenyl |
| 365. | CH₂S(O)₂R³ | 4-CH₃C(O)-phenyl |
| 366. | CH₂S(O)₂R³ | 4-CH₃OC(O)-phenyl |
| 367. | CH₂S(O)₂R³ | 4-CH₃OS(O)₂-phenyl |
| 368. | CH₂S(O)₂R³ | 4-H₂NC(O)-phenyl |
| 369. | CH₂S(O)₂R³ | 4-H₂NS(O)₂-phenyl |
| 370. | CH₂S(O)₂R³ | 4-N-piperdino-C(O)-phenyl |
| 371. | CH₂S(O)₂R³ | 4-N-pyrrolidino-C(O)-phenyl |
| 372. | CH₂S(O)₂R³ | 4-N-piperdino-S(O)₂-phenyl |
| 373. | CH₂S(O)₂R³ | 4-N-pyrrolidino-S(O)₂-phenyl |
| 374. | CH₂S(O)₂R³ | Phen-2-yl |
| 375. | CH₂S(O)₂R³ | 5-NO₂-benzothiazol-2-yl |
| 376. | CH₂S(O)₂R³ | 5-NH₂-benzothiazol-2-yl |
| 377. | CH₂S(O)₂R³ | 5-Cl-benzothiazol-2-yl |
| 378. | CH₂S(O)₂R³ | 5-cyano-benzothiazol-2-yl |
| 379. | CH₂S(O)₂R³ | 5-CH₃-benzothiazol-2-yl |
| 380. | CH₂S(O)₂R³ | 5-CF₃-benzothiazol-2-yl |
| 381. | CH₂S(O)₂R³ | 5-CH₃O-benzothiazol-2-yl |
| 382. | CH₂S(O)₂R³ | 5-CH₃C(O)-benzothiazol-2-yl |
| 383. | CH₂S(O)₂R³ | 5-CH₃OC(O)-benzothiazol-2-yl |
| 384. | CH₂S(O)₂R³ | 5-CH₃OS(O)₂-benzothiazol-2-yl |
| 385. | CH₂S(O)₂R³ | 5-H₂NC(O)-benzothiazol-2-yl |
| 386. | CH₂S(O)₂R³ | 5-H₂NS(O)₂-benzothiazol-2-yl |
| 387. | CH₂S(O)₂R³ | 5-N-piperdino-C(O)-benzothiazol-2-yl |
| 388. | CH₂S(O)₂R³ | 5-N-pyrrolidino-C(O)-benzothiazol-2-yl |
| 389. | CH₂S(O)₂R³ | 5-N-piperdino-S(O)₂-benzothiazol-2-yl |
| 390. | CH₂S(O)₂R³ | 5-N-pyrrolidino-S(O)₂-benzothiazol-2-yl |
| 391. | CH₂S(O)₂R³ | Benzothiazol-2-yl |
| 392. | CH₂S(O)₂R³ | 5-NO₂-benzimidazol-2-yl |
| 393. | CH₂S(O)₂R³ | 5-NH₂-benzimidazol-2-yl |
| 394. | CH₂S(O)₂R³ | 5-Cl-benzimidazol-2-yl |
| 395. | CH₂S(O)₂R³ | 5-cyano-benzimidazol-2-yl |
| 396. | CH₂S(O)₂R³ | 5-CH₃-benzimidazol-2-yl |
| 397. | CH₂S(O)₂R³ | 5-CF₃-benzimidazol-2-yl |
| 398. | CH₂S(O)₂R³ | 5-CH₃O-benzimidazol-2-yl |
| 399. | CH₂S(O)₂R³ | 5-CH₃C(O)-benzimidazol-2-yl |

TABLE 2-continued

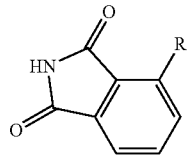

| Ex. # | R | R³ |
|---|---|---|
| 400. | CH₂S(O)₂R³ | 5-CH₃OC(O)-benzimidazol-2-yl |
| 401. | CH₂S(O)₂R³ | 5-CH₃OS(O)₂-benzimidazol-2-yl |
| 402. | CH₂S(O)₂R³ | 5-H₂NC(O)-benzimidazol-2-yl |
| 403. | CH₂S(O)₂R³ | 5-H₂NS(O)₂-benzimidazol-2-yl |
| 404. | CH₂S(O)₂R³ | 5-N-piperdino-C(O)-benzimidazol-2-yl |
| 405. | CH₂S(O)₂R³ | 5-N-pyrrolidino-C(O)-benzimidazol-2-yl |
| 406. | CH₂S(O)₂R³ | 5-N-piperdino-S(O)₂-benzimidazol-2-yl |
| 407. | CH₂S(O)₂R³ | 5-N-pyrrolidino-S(O)₂-benzimidazol-2-yl |
| 408. | CH₂S(O)₂R³ | Benzimidazol-2-yl |

TABLE 3

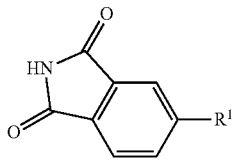

| Ex. # | R | R³ |
|---|---|---|
| 1. | NHC(O)R³ | 5-NO₂-furan-2-yl |
| 2. | NHC(O)R³ | 5-NH₂-furan-2-yl |
| 3. | NHC(O)R³ | 5-Cl-furan-2-yl |
| 4. | NHC(O)R³ | 5-cyano-furan-2-yl |
| 5. | NHC(O)R³ | 5-CH₃-furan-2-yl |
| 6. | NHC(O)R³ | 5-CF₃-furan-2-yl |
| 7. | NHC(O)R³ | 5-CH₃O-furan-2-yl |
| 8. | NHC(O)R³ | 5-CH₃C(O)-furan-2-yl |
| 9. | NHC(O)R³ | 5-CH₃OC(O)-furan-2-yl |
| 10. | NHC(O)R³ | 5-CH₃OS(O)₂-furan-2-yl |
| 11. | NHC(O)R³ | 5-H₂NC(O)-furan-2-yl |
| 12. | NHC(O)R³ | 5-H₂NS(O)₂-furan-2-yl |
| 13. | NHC(O)R³ | 5-N-piperdino-C(O)-furan-2-yl |
| 14. | NHC(O)R³ | 5-N-pyrrolidino-C(O)-furan-2-yl |
| 15. | NHC(O)R³ | 5-N-piperdino-S(O)₂-furan-2-yl |
| 16. | NHC(O)R³ | 5-N-pyrrolidino-S(O)₂-furan-2-yl |
| 17. | NHC(O)R³ | Furan-2-yl |
| 18. | NHC(O)R³ | 5-NO₂-thien-2-yl |
| 19. | NHC(O)R³ | 5-NH₂-thien-2-yl |
| 20. | NHC(O)R³ | 5-Cl-thien-2-yl |
| 21. | NHC(O)R³ | 5-cyano-thien-2-yl |
| 22. | NHC(O)R³ | 5-CH₃-thien-2-yl |
| 23. | NHC(O)R³ | 5-CF₃-thien-2-yl |
| 24. | NHC(O)R³ | 5-CH₃O-thien-2-yl |
| 25. | NHC(O)R³ | 5-CH₃C(O)-thien-2-yl |
| 26. | NHC(O)R³ | 5-CH₃OC(O)-thien-2-yl |
| 27. | NHC(O)R³ | 5-CH₃OS(O)₂-thien-2-yl |
| 28. | NHC(O)R³ | 5-H₂NC(O)-thien-2-yl |
| 29. | NHC(O)R³ | 5-H₂NS(O)₂-thien-2-yl |
| 30. | NHC(O)R³ | 5-N-piperdino-C(O)-thien-2-yl |
| 31. | NHC(O)R³ | 5-N-pyrrolidino-C(O)-thien-2-yl |
| 32. | NHC(O)R³ | 5-N-piperdino-S(O)₂-thien-2-yl |
| 33. | NHC(O)R³ | 5-N-pyrrolidino-S(O)₂-thien-2-yl |
| 34. | NHC(O)R³ | Thien-2-yl |
| 35. | NHC(O)R³ | 5-NO₂-pyrrol-2-yl |
| 36. | NHC(O)R³ | 5-NH₂-pyrrol-2-yl |
| 37. | NHC(O)R³ | 5-Cl-pyrrol-2-yl |
| 38. | NHC(O)R³ | 5-cyano-pyrrol-2-yl |
| 39. | NHC(O)R³ | 5-CH₃-pyrrol-2-yl |
| 40. | NHC(O)R³ | 5-CF₃-pyrrol-2-yl |
| 41. | NHC(O)R³ | 5-CH₃O-pyrrol-2-yl |

TABLE 3-continued

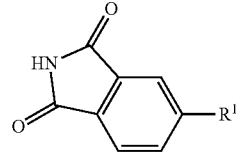

| Ex. # | R | R³ |
|---|---|---|
| 42. | NHC(O)R³ | 5-CH₃C(O)-pyrrol-2-yl |
| 43. | NHC(O)R³ | 5-CH₃OC(O)-pyrrol-2-yl |
| 44. | NHC(O)R³ | 5-CH₃OS(O)₂-pyrrol-2-yl |
| 45. | NHC(O)R³ | 5-H₂NC(O)-pyrrol-2-yl |
| 46. | NHC(O)R³ | 5-H₂NS(O)₂-pyrrol-2-yl |
| 47. | NHC(O)R³ | 5-N-piperdino-C(O)-pyrrol-2-yl |
| 48. | NHC(O)R³ | 5-N-pyrrolidino-C(O)-pyrrol-2-yl |
| 49. | NHC(O)R³ | 5-N-piperdino-S(O)₂-pyrrol-2-yl |
| 50. | NHC(O)R³ | 5-N-pyrrolidino-S(O)₂-pyrrol-2-yl |
| 51. | NHC(O)R³ | Pyrrol-2-yl |
| 52. | NHC(O)R³ | 4-NO₂-phenyl |
| 53. | NHC(O)R³ | 4-NH₂-phenyl |
| 54. | NHC(O)R³ | 4-Cl-phenyl |
| 55. | NHC(O)R³ | 4-cyano-phenyl |
| 56. | NHC(O)R³ | 4-CH₃-phenyl |
| 57. | NHC(O)R³ | 4-CF₃-phenyl |
| 58. | NHC(O)R³ | 4-CH₃O-phenyl |
| 59. | NHC(O)R³ | 4-CH₃C(O)-phenyl |
| 60. | NHC(O)R³ | 4-CH₃OC(O)-phenyl |
| 61. | NHC(O)R³ | 4-CH₃OS(O)₂-phenyl |
| 62. | NHC(O)R³ | 4-H₂NC(O)-phenyl |
| 63. | NHC(O)R³ | 4-H₂NS(O)₂-phenyl |
| 64. | NHC(O)R³ | 4-N-piperdino-C(O)-phenyl |
| 65. | NHC(O)R³ | 4-N-pyrrolidino-C(O)-phenyl |
| 66. | NHC(O)R³ | 4-N-piperdino-S(O)₂-phenyl |
| 67. | NHC(O)R³ | 4-N-pyrrolidino-S(O)₂-phenyl |
| 68. | NHC(O)R³ | Phen-2-yl |
| 69. | NHC(O)R³ | 5-NO₂-benzothiazol-2-yl |
| 70. | NHC(O)R³ | 5-NH₂-benzothiazol-2-yl |
| 71. | NHC(O)R³ | 5-Cl-benzothiazol-2-yl |
| 72. | NHC(O)R³ | 5-cyano-benzothiazol-2-yl |
| 73. | NHC(O)R³ | 5-CH₃-benzothiazol-2-yl |
| 74. | NHC(O)R³ | 5-CF₃-benzothiazol-2-yl |
| 75. | NHC(O)R³ | 5-CH₃O-benzothiazol-2-yl |
| 76. | NHC(O)R³ | 5-CH₃C(O)-benzothiazol-2-yl |
| 77. | NHC(O)R³ | 5-CH₃OC(O)-benzothiazol-2-yl |
| 78. | NHC(O)R³ | 5-CH₃OS(O)₂-benzothiazol-2-yl |
| 79. | NHC(O)R³ | 5-H₂NC(O)-benzothiazol-2-yl |
| 80. | NHC(O)R³ | 5-H₂NS(O)₂-benzothiazol-2-yl |
| 81. | NHC(O)R³ | 5-N-piperdino-C(O)-benzothiazol-2-yl |
| 82. | NHC(O)R³ | 5-N-pyrrolidino-C(O)-benzothiazol-2-yl |
| 83. | NHC(O)R³ | 5-N-piperdino-S(O)₂-benzothiazol-2-yl |
| 84. | NHC(O)R³ | 5-N-pyrrolidino-S(O)₂-benzothiazol-2-yl |
| 85. | NHC(O)R³ | Benzothiazol-2-yl |
| 86. | NHC(O)R³ | 5-NO₂-benzimidazol-2-yl |
| 87. | NHC(O)R³ | 5-NH₂-benzimidazol-2-yl |
| 88. | NHC(O)R³ | 5-Cl-benzimidazol-2-yl |
| 89. | NHC(O)R³ | 5-cyano-benzimidazol-2-yl |
| 90. | NHC(O)R³ | 5-CH₃-benzimidazol-2-yl |
| 91. | NHC(O)R³ | 5-CF₃-benzimidazol-2-yl |
| 92. | NHC(O)R³ | 5-CH₃O-benzimidazol-2-yl |
| 93. | NHC(O)R³ | 5-CH₃C(O)-benzimidazol-2-yl |
| 94. | NHC(O)R³ | 5-CH₃OC(O)-benzimidazol-2-yl |
| 95. | NHC(O)R³ | 5-CH₃OS(O)₂-benzimidazol-2-yl |
| 96. | NHC(O)R³ | 5-H₂NC(O)-benzimidazol-2-yl |
| 97. | NHC(O)R³ | 5-H₂NS(O)₂-benzimidazol-2-yl |
| 98. | NHC(O)R³ | 5-N-piperdino-C(O)-benzimidazol-2-yl |
| 99. | NHC(O)R³ | 5-N-pyrrolidino-C(O)-benzimidazol-2-yl |
| 100. | NHC(O)R³ | 5-N-piperdino-S(O)₂-benzimidazol-2-yl |
| 101. | NHC(O)R³ | 5-N-pyrrolidino-S(O)₂-benzimidazol-2-yl |
| 102. | NHC(O)R³ | Benzimidazol-2-yl |
| 103. | NHS(O)₂R³ | 5-NO₂-furan-2-yl |
| 104. | NHS(O)₂R³ | 5-NH₂-furan-2-yl |
| 105. | NHS(O)₂R³ | 5-Cl-furan-2-yl |
| 106. | NHS(O)₂R³ | 5-cyano-furan-2-yl |
| 107. | NHS(O)₂R³ | 5-CH₃-furan-2-yl |
| 108. | NHS(O)₂R³ | 5-CF₃-furan-2-yl |

TABLE 3-continued

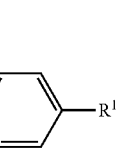

| Ex. # | R | R³ |
|---|---|---|
| 109. | NHS(O)₂R³ | 5-CH₃O-furan-2-yl |
| 110. | NHS(O)₂R³ | 5-CH₃C(O)-furan-2-yl |
| 111. | NHS(O)₂R³ | 5-CH₃OC(O)-furan-2-yl |
| 112. | NHS(O)₂R³ | 5-CH₃OS(O)₂-furan-2-yl |
| 113. | NHS(O)₂R³ | 5-H₂NC(O)-furan-2-yl |
| 114. | NHS(O)₂R³ | 5-H₂NS(O)₂-furan-2-yl |
| 115. | NHS(O)₂R³ | 5-N-piperdino-C(O)-furan-2-yl |
| 116. | NHS(O)₂R³ | 5-N-pyrrolidino-C(O)-furan-2-yl |
| 117. | NHS(O)₂R³ | 5-N-piperdino-S(O)₂-furan-2-yl |
| 118. | NHS(O)₂R³ | 5-N-pyrrolidino-S(O)₂-furan-2-yl |
| 119. | NHS(O)₂R³ | Furan-2-yl |
| 120. | NHS(O)₂R³ | 5-NO₂-thien-2-yl |
| 121. | NHS(O)₂R³ | 5-NH₂-thien-2-yl |
| 122. | NHS(O)₂R³ | 5-Cl-thien-2-yl |
| 123. | NHS(O)₂R³ | 5-cyano-thien-2-yl |
| 124. | NHS(O)₂R³ | 5-CH₃-thien-2-yl |
| 125. | NHS(O)₂R³ | 5-CF₃-thien-2-yl |
| 126. | NHS(O)₂R³ | 5-CH₃O-thien-2-yl |
| 127. | NHS(O)₂R³ | 5-CH₃C(O)-thien-2-yl |
| 128. | NHS(O)₂R³ | 5-CH₃OC(O)-thien-2-yl |
| 129. | NHS(O)₂R³ | 5-CH₃OS(O)₂-thien-2-yl |
| 130. | NHS(O)₂R³ | 5-H₂NC(O)-thien-2-yl |
| 131. | NHS(O)₂R³ | 5-H₂NS(O)₂-thien-2-yl |
| 132. | NHS(O)₂R³ | 5-N-piperdino-C(O)-thien-2-yl |
| 133. | NHS(O)₂R³ | 5-N-pyrrolidino-C(O)-thien-2-yl |
| 134. | NHS(O)₂R³ | 5-N-piperdino-S(O)₂-thien-2-yl |
| 135. | NHS(O)₂R³ | 5-N-pyrrolidino-S(O)₂-thien-2-yl |
| 136. | NHS(O)₂R³ | Thien-2-yl |
| 137. | NHS(O)₂R³ | 5-NO₂-pyrrol-2-yl |
| 138. | NHS(O)₂R³ | 5-NH₂-pyrrol-2-yl |
| 139. | NHS(O)₂R³ | 5-Cl-pyrrol-2-yl |
| 140. | NHS(O)₂R³ | 5-cyano-pyrrol-2-yl |
| 141. | NHS(O)₂R³ | 5-CH₃-pyrrol-2-yl |
| 142. | NHS(O)₂R³ | 5-CF₃-pyrrol-2-yl |
| 143. | NHS(O)₂R³ | 5-CH₃O-pyrrol-2-yl |
| 144. | NHS(O)₂R³ | 5-CH₃C(O)-pyrrol-2-yl |
| 145. | NHS(O)₂R³ | 5-CH₃OC(O)-pyrrol-2-yl |
| 146. | NHS(O)₂R³ | 5-CH₃OS(O)₂-pyrrol-2-yl |
| 147. | NHS(O)₂R³ | 5-H₂NC(O)-pyrrol-2-yl |
| 148. | NHS(O)₂R³ | 5-H₂NS(O)₂-pyrrol-2-yl |
| 149. | NHS(O)₂R³ | 5-N-piperdino-C(O)-pyrrol-2-yl |
| 150. | NHS(O)₂R³ | 5-N-pyrrolidino-C(O)-pyrrol-2-yl |
| 151. | NHS(O)₂R³ | 5-N-piperdino-S(O)₂-pyrrol-2-yl |
| 152. | NHS(O)₂R³ | 5-N-pyrrolidino-S(O)₂-pyrrol-2-yl |
| 153. | NHS(O)₂R³ | Pyrrol-2-yl |
| 154. | NHS(O)₂R³ | 4-NO₂-phenyl |
| 155. | NHS(O)₂R³ | 4-NH₂-phenyl |
| 156. | NHS(O)₂R³ | 4-Cl-phenyl |
| 157. | NHS(O)₂R³ | 4-cyano-phenyl |
| 158. | NHS(O)₂R³ | 4-CH₃-phenyl |
| 159. | NHS(O)₂R³ | 4-CF₃-phenyl |
| 160. | NHS(O)₂R³ | 4-CH₃O-phenyl |
| 161. | NHS(O)₂R³ | 4-CH₃C(O)-phenyl |
| 162. | NHS(O)₂R³ | 4-CH₃OC(O)-phenyl |
| 163. | NHS(O)₂R³ | 4-CH₃OS(O)₂-phenyl |
| 164. | NHS(O)₂R³ | 4-H₂NC(O)-phenyl |
| 165. | NHS(O)₂R³ | 4-H₂NS(O)₂-phenyl |
| 166. | NHS(O)₂R³ | 4-N-piperdino-C(O)-phenyl |
| 167. | NHS(O)₂R³ | 4-N-pyrrolidino-C(O)-phenyl |
| 168. | NHS(O)₂R³ | 4-N-piperdino-S(O)₂-phenyl |
| 169. | NHS(O)₂R³ | 4-N-pyrrolidino-S(O)₂-phenyl |
| 170. | NHS(O)₂R³ | Phen-2-yl |
| 171. | NHS(O)₂R³ | 5-NO₂-benzothiazol-2-yl |
| 172. | NHS(O)₂R³ | 5-NH₂-benzothiazol-2-yl |
| 173. | NHS(O)₂R³ | 5-Cl-benzothiazol-2-yl |
| 174. | NHS(O)₂R³ | 5-cyano-benzothiazol-2-yl |
| 175. | NHS(O)₂R³ | 5-CH₃-benzothiazol-2-yl |

TABLE 3-continued

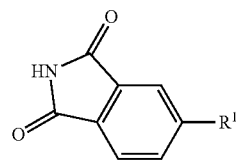

| Ex. # | R | R³ |
|---|---|---|
| 176. | NHS(O)₂R³ | 5-CF₃-benzothiazol-2-yl |
| 177. | NHS(O)₂R³ | 5-CH₃O-benzothiazol-2-yl |
| 178. | NHS(O)₂R³ | 5-CH₃C(O)-benzothiazol-2-yl |
| 179. | NHS(O)₂R³ | 5-CH₃OC(O)-benzothiazol-2-yl |
| 180. | NHS(O)₂R³ | 5-CH₃OS(O)₂-benzothiazol-2-yl |
| 181. | NHS(O)₂R³ | 5-H₂NC(O)-benzothiazol-2-yl |
| 182. | NHS(O)₂R³ | 5-H₂NS(O)₂-benzothiazol-2-yl |
| 183. | NHS(O)₂R³ | 5-N-piperdino-C(O)-benzothiazol-2-yl |
| 184. | NHS(O)₂R³ | 5-N-pyrrolidino-C(O)-benzothiazol-2-yl |
| 185. | NHS(O)₂R³ | 5-N-piperdino-S(O)₂-benzothiazol-2-yl |
| 186. | NHS(O)₂R³ | 5-N-pyrrolidino-S(O)₂-benzothiazol-2-yl |
| 187. | NHS(O)₂R³ | Benzothiazol-2-yl |
| 188. | NHS(O)₂R³ | 5-NO₂-benzimidazol-2-yl |
| 189. | NHS(O)₂R³ | 5-NH₂-benzimidazol-2-yl |
| 190. | NHS(O)₂R³ | 5-Cl-benzimidazol-2-yl |
| 191. | NHS(O)₂R³ | 5-cyano-benzimidazol-2-yl |
| 192. | NHS(O)₂R³ | 5-CH₃-benzimidazol-2-yl |
| 193. | NHS(O)₂R³ | 5-CF₃-benzimidazol-2-yl |
| 194. | NHS(O)₂R³ | 5-CH₃O-benzimidazol-2-yl |
| 195. | NHS(O)₂R³ | 5-CH₃C(O)-benzimidazol-2-yl |
| 196. | NHS(O)₂R³ | 5-CH₃OC(O)-benzimidazol-2-yl |
| 197. | NHS(O)₂R³ | 5-CH₃OS(O)₂-benzimidazol-2-yl |
| 198. | NHS(O)₂R³ | 5-H₂NC(O)-benzimidazol-2-yl |
| 199. | NHS(O)₂R³ | 5-H₂NS(O)₂-benzimidazol-2-yl |
| 200. | NHS(O)₂R³ | 5-N-piperdino-C(O)-benzimidazol-2-yl |
| 201. | NHS(O)₂R³ | 5-N-pyrrolidino-C(O)-benzimidazol-2-yl |
| 202. | NHS(O)₂R³ | 5-N-piperdino-S(O)₂-benzimidazol-2-yl |
| 203. | NHS(O)₂R³ | 5-N-pyrrolidino-S(O)₂-benzimidazol-2-yl |
| 204. | NHS(O)₂R³ | Benzimidazol-2-yl |
| 205. | CH₂C(O)R³ | 5-NO₂-furan-2-yl |
| 206. | CH₂C(O)R³ | 5-NH₂-furan-2-yl |
| 207. | CH₂C(O)R³ | 5-Cl-furan-2-yl |
| 208. | CH₂C(O)R³ | 5-cyano-furan-2-yl |
| 209. | CH₂C(O)R³ | 5-CH₃-furan-2-yl |
| 210. | CH₂C(O)R³ | 5-CF₃-furan-2-yl |
| 211. | CH₂C(O)R³ | 5-CH₃O-furan-2-yl |
| 212. | CH₂C(O)R³ | 5-CH₃C(O)-furan-2-yl |
| 213. | CH₂C(O)R³ | 5-CH₃OC(O)-furan-2-yl |
| 214. | CH₂C(O)R³ | 5-CH₃OS(O)₂-furan-2-yl |
| 215. | CH₂C(O)R³ | 5-H₂NC(O)-furan-2-yl |
| 216. | CH₂C(O)R³ | 5-H₂NS(O)₂-furan-2-yl |
| 217. | CH₂C(O)R³ | 5-N-piperdino-C(O)-furan-2-yl |
| 218. | CH₂C(O)R³ | 5-N-pyrrolidino-C(O)-furan-2-yl |
| 219. | CH₂C(O)R³ | 5-N-piperdino-S(O)₂-furan-2-yl |
| 220. | CH₂C(O)R³ | 5-N-pyrrolidino-S(O)₂-furan-2-yl |
| 221. | CH₂C(O)R³ | Furan-2-yl |
| 222. | CH₂C(O)R³ | 5-NO₂-thien-2-yl |
| 223. | CH₂C(O)R³ | 5-NH₂-thien-2-yl |
| 224. | CH₂C(O)R³ | 5-Cl-thien-2-yl |
| 225. | CH₂C(O)R³ | 5-cyano-thien-2-yl |
| 226. | CH₂C(O)R³ | 5-CH₃-thien-2-yl |
| 227. | CH₂C(O)R³ | 5-CF₃-thien-2-yl |
| 228. | CH₂C(O)R³ | 5-CH₃O-thien-2-yl |
| 229. | CH₂C(O)R³ | 5-CH₃C(O)-thien-2-yl |
| 230. | CH₂C(O)R³ | 5-CH₃OC(O)-thien-2-yl |
| 231. | CH₂C(O)R³ | 5-CH₃OS(O)₂-thien-2-yl |
| 232. | CH₂C(O)R³ | 5-H₂NC(O)-thien-2-yl |
| 233. | CH₂C(O)R³ | 5-H₂NS(O)₂-thien-2-yl |
| 234. | CH₂C(O)R³ | 5-N-piperdino-C(O)-thien-2-yl |
| 235. | CH₂C(O)R³ | 5-N-pyrrolidino-C(O)-thien-2-yl |
| 236. | CH₂C(O)R³ | 5-N-piperdino-S(O)₂-thien-2-yl |
| 237. | CH₂C(O)R³ | 5-N-pyrrolidino-S(O)₂-thien-2-yl |
| 238. | CH₂C(O)R³ | Thien-2-yl |
| 239. | CH₂C(O)R³ | 5-NO₂-pyrrol-2-yl |
| 240. | CH₂C(O)R³ | 5-NH₂-pyrrol-2-yl |
| 241. | CH₂C(O)R³ | 5-Cl-pyrrol-2-yl |
| 242. | CH₂C(O)R³ | 5-cyano-pyrrol-2-yl |

TABLE 3-continued

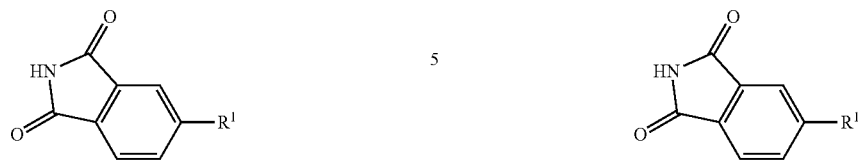

| Ex. # | R | R³ |
|---|---|---|
| 243. | CH₂C(O)R³ | 5-CH₃-pyrrol-2-yl |
| 244. | CH₂C(O)R³ | 5-CF₃-pyrrol-2-yl |
| 245. | CH₂C(O)R³ | 5-CH₃O-pyrrol-2-yl |
| 246. | CH₂C(O)R³ | 5-CH₃C(O)-pyrrol-2-yl |
| 247. | CH₂C(O)R³ | 5-CH₃OC(O)-pyrrol-2-yl |
| 248. | CH₂C(O)R³ | 5-CH₃OS(O)₂-pyrrol-2-yl |
| 249. | CH₂C(O)R³ | 5-H₂NC(O)-pyrrol-2-yl |
| 250. | CH₂C(O)R³ | 5-H₂NS(O)₂-pyrrol-2-yl |
| 251. | CH₂C(O)R³ | 5-N-piperdino-C(O)-pyrrol-2-yl |
| 252. | CH₂C(O)R³ | 5-N-pyrrolidino-C(O)-pyrrol-2-yl |
| 253. | CH₂C(O)R³ | 5-N-piperdino-S(O)₂-pyrrol-2-yl |
| 254. | CH₂C(O)R³ | 5-N-pyrrolidino-S(O)₂-pyrrol-2-yl |
| 255. | CH₂C(O)R³ | Pyrrol-2-yl |
| 256. | CH₂C(O)R³ | 4-NO₂-phenyl |
| 257. | CH₂C(O)R³ | 4-NH₂-phenyl |
| 258. | CH₂C(O)R³ | 4-Cl-phenyl |
| 259. | CH₂C(O)R³ | 4-cyano-phenyl |
| 260. | CH₂C(O)R³ | 4-CH₃-phenyl |
| 261. | CH₂C(O)R³ | 4-CF₃-phenyl |
| 262. | CH₂C(O)R³ | 4-CH₃O-phenyl |
| 263. | CH₂C(O)R³ | 4-CH₃C(O)-phenyl |
| 264. | CH₂C(O)R³ | 4-CH₃OC(O)-phenyl |
| 265. | CH₂C(O)R³ | 4-CH₃OS(O)₂-phenyl |
| 266. | CH₂C(O)R³ | 4-H₂NC(O)-phenyl |
| 267. | CH₂C(O)R³ | 4-H₂NS(O)₂-phenyl |
| 268. | CH₂C(O)R³ | 4-N-piperdino-C(O)-phenyl |
| 269. | CH₂C(O)R³ | 4-N-pyrrolidino-C(O)-phenyl |
| 270. | CH₂C(O)R³ | 4-N-piperdino-S(O)₂-phenyl |
| 271. | CH₂C(O)R³ | 4-N-pyrrolidino-S(O)₂-phenyl |
| 272. | CH₂C(O)R³ | Phen-2-yl |
| 273. | CH₂C(O)R³ | 5-NO₂-benzothiazol-2-yl |
| 274. | CH₂C(O)R³ | 5-NH₂-benzothiazol-2-yl |
| 275. | CH₂C(O)R³ | 5-Cl-benzothiazol-2-yl |
| 276. | CH₂C(O)R³ | 5-cyano-benzothiazol-2-yl |
| 277. | CH₂C(O)R³ | 5-CH₃-benzothiazol-2-yl |
| 278. | CH₂C(O)R³ | 5-CF₃-benzothiazol-2-yl |
| 279. | CH₂C(O)R³ | 5-CH₃O-benzothiazol-2-yl |
| 280. | CH₂C(O)R³ | 5-CH₃C(O)-benzothiazol-2-yl |
| 281. | CH₂C(O)R³ | 5-CH₃OC(O)-benzothiazol-2-yl |
| 282. | CH₂C(O)R³ | 5-CH₃OS(O)₂-benzothiazol-2-yl |
| 283. | CH₂C(O)R³ | 5-H₂NC(O)-benzothiazol-2-yl |
| 284. | CH₂C(O)R³ | 5-H₂NS(O)₂-benzothiazol-2-yl |
| 285. | CH₂C(O)R³ | 5-N-piperdino-C(O)-benzothiazol-2-yl |
| 286. | CH₂C(O)R³ | 5-N-pyrrolidino-C(O)-benzothiazol-2-yl |
| 287. | CH₂C(O)R³ | 5-N-piperdino-S(O)₂-benzothiazol-2-yl |
| 288. | CH₂C(O)R³ | 5-N-pyrrolidino-S(O)₂-benzothiazol-2-yl |
| 289. | CH₂C(O)R³ | Benzothiazol-2-yl |
| 290. | CH₂C(O)R³ | 5-NO₂-benzimidazol-2-yl |
| 291. | CH₂C(O)R³ | 5-NH₂-benzimidazol-2-yl |
| 292. | CH₂C(O)R³ | 5-Cl-benzimidazol-2-yl |
| 293. | CH₂C(O)R³ | 5-cyano-benzimidazol-2-yl |
| 294. | CH₂C(O)R³ | 5-CH₃-benzimidazol-2-yl |
| 295. | CH₂C(O)R³ | 5-CF₃-benzimidazol-2-yl |
| 296. | CH₂C(O)R³ | 5-CH₃O-benzimidazol-2-yl |
| 297. | CH₂C(O)R³ | 5-CH₃C(O)-benzimidazol-2-yl |
| 298. | CH₂C(O)R³ | 5-CH₃OC(O)-benzimidazol-2-yl |
| 299. | CH₂C(O)R³ | 5-CH₃OS(O)₂-benzimidazol-2-yl |
| 300. | CH₂C(O)R³ | 5-H₂NC(O)-benzimidazol-2-yl |
| 301. | CH₂C(O)R³ | 5-H₂NS(O)₂-benzimidazol-2-yl |
| 302. | CH₂C(O)R³ | 5-N-piperdino-C(O)-benzimidazol-2-yl |
| 303. | CH₂C(O)R³ | 5-N-pyrrolidino-C(O)-benzimidazol-2-yl |
| 304. | CH₂C(O)R³ | 5-N-piperdino-S(O)₂-benzimidazol-2-yl |
| 305. | CH₂C(O)R³ | 5-N-pyrrolidino-S(O)₂-benzimidazol-2-yl |
| 306. | CH₂C(O)R³ | Benzimidazol-2-yl |
| 307. | CH₂S(O)₂R³ | 5-NO₂-furan-2-yl |
| 308. | CH₂S(O)₂R³ | 5-NH₂-furan-2-yl |
| 309. | CH₂S(O)₂R³ | 5-Cl-furan-2-yl |

TABLE 3-continued

| Ex. # | R | R³ |
|---|---|---|
| 310. | CH₂S(O)₂R³ | 5-cyano-furan-2-yl |
| 311. | CH₂S(O)₂R³ | 5-CH₃-furan-2-yl |
| 312. | CH₂S(O)₂R³ | 5-CF₃-furan-2-yl |
| 313. | CH₂S(O)₂R³ | 5-CH₃O-furan-2-yl |
| 314. | CH₂S(O)₂R³ | 5-CH₃C(O)-furan-2-yl |
| 315. | CH₂S(O)₂R³ | 5-CH₃OC(O)-furan-2-yl |
| 316. | CH₂S(O)₂R³ | 5-CH₃OS(O)₂-furan-2-yl |
| 317. | CH₂S(O)₂R³ | 5-H₂NC(O)-furan-2-yl |
| 318. | CH₂S(O)₂R³ | 5-H₂NS(O)₂-furan-2-yl |
| 319. | CH₂S(O)₂R³ | 5-N-piperdino-C(O)-furan-2-yl |
| 320. | CH₂S(O)₂R³ | 5-N-pyrrolidino-C(O)-furan-2-yl |
| 321. | CH₂S(O)₂R³ | 5-N-piperdino-S(O)₂-furan-2-yl |
| 322. | CH₂S(O)₂R³ | 5-N-pyrrolidino-S(O)₂-furan-2-yl |
| 323. | CH₂S(O)₂R³ | Furan-2-yl |
| 324. | CH₂S(O)₂R³ | 5-NO₂-thien-2-yl |
| 325. | CH₂S(O)₂R³ | 5-NH₂-thien-2-yl |
| 326. | CH₂S(O)₂R³ | 5-Cl-thien-2-yl |
| 327. | CH₂S(O)₂R³ | 5-cyano-thien-2-yl |
| 328. | CH₂S(O)₂R³ | 5-CH₃-thien-2-yl |
| 329. | CH₂S(O)₂R³ | 5-CF₃-thien-2-yl |
| 330. | CH₂S(O)₂R³ | 5-CH₃O-thien-2-yl |
| 331. | CH₂S(O)₂R³ | 5-CH₃C(O)-thien-2-yl |
| 332. | CH₂S(O)₂R³ | 5-CH₃OC(O)-thien-2-yl |
| 333. | CH₂S(O)₂R³ | 5-CH₃OS(O)₂-thien-2-yl |
| 334. | CH₂S(O)₂R³ | 5-H₂NC(O)-thien-2-yl |
| 335. | CH₂S(O)₂R³ | 5-H₂NS(O)₂-thien-2-yl |
| 336. | CH₂S(O)₂R³ | 5-N-piperdino-C(O)-thien-2-yl |
| 337. | CH₂S(O)₂R³ | 5-N-pyrrolidino-C(O)-thien-2-yl |
| 338. | CH₂S(O)₂R³ | 5-N-piperdino-S(O)₂-thien-2-yl |
| 339. | CH₂S(O)₂R³ | 5-N-pyrrolidino-S(O)₂-thien-2-yl |
| 340. | CH₂S(O)₂R³ | Thien-2-yl |
| 341. | CH₂S(O)₂R³ | 5-NO₂-pyrrol-2-yl |
| 342. | CH₂S(O)₂R³ | 5-NH₂-pyrrol-2-yl |
| 343. | CH₂S(O)₂R³ | 5-Cl-pyrrol-2-yl |
| 344. | CH₂S(O)₂R³ | 5-cyano-pyrrol-2-yl |
| 345. | CH₂S(O)₂R³ | 5-CH₃-pyrrol-2-yl |
| 346. | CH₂S(O)₂R³ | 5-CF₃-pyrrol-2-yl |
| 347. | CH₂S(O)₂R³ | 5-CH₃O-pyrrol-2-yl |
| 348. | CH₂S(O)₂R³ | 5-CH₃C(O)-pyrrol-2-yl |
| 349. | CH₂S(O)₂R³ | 5-CH₃OC(O)-pyrrol-2-yl |
| 350. | CH₂S(O)₂R³ | 5-CH₃OS(O)₂-pyrrol-2-yl |
| 351. | CH₂S(O)₂R³ | 5-H₂NC(O)-pyrrol-2-yl |
| 352. | CH₂S(O)₂R³ | 5-H₂NS(O)₂-pyrrol-2-yl |
| 353. | CH₂S(O)₂R³ | 5-N-piperdino-C(O)-pyrrol-2-yl |
| 354. | CH₂S(O)₂R³ | 5-N-pyrrolidino-C(O)-pyrrol-2-yl |
| 355. | CH₂S(O)₂R³ | 5-N-piperdino-S(O)₂-pyrrol-2-yl |
| 356. | CH₂S(O)₂R³ | 5-N-pyrrolidino-S(O)₂-pyrrol-2-yl |
| 357. | CH₂S(O)₂R³ | Pyrrol-2-yl |
| 358. | CH₂S(O)₂R³ | 4-NO₂-phenyl |
| 359. | CH₂S(O)₂R³ | 4-NH₂-phenyl |
| 360. | CH₂S(O)₂R³ | 4-Cl-phenyl |
| 361. | CH₂S(O)₂R³ | 4-cyano-phenyl |
| 362. | CH₂S(O)₂R³ | 4-CH₃-phenyl |
| 363. | CH₂S(O)₂R³ | 4-CF₃-phenyl |
| 364. | CH₂S(O)₂R³ | 4-CH₃O-phenyl |
| 365. | CH₂S(O)₂R³ | 4-CH₃C(O)-phenyl |
| 366. | CH₂S(O)₂R³ | 4-CH₃OC(O)-phenyl |
| 367. | CH₂S(O)₂R³ | 4-CH₃OS(O)₂-phenyl |
| 368. | CH₂S(O)₂R³ | 4-H₂NC(O)-phenyl |
| 369. | CH₂S(O)₂R³ | 4-H₂NS(O)₂-phenyl |
| 370. | CH₂S(O)₂R³ | 4-N-piperdino-C(O)-phenyl |
| 371. | CH₂S(O)₂R³ | 4-N-pyrrolidino-C(O)-phenyl |
| 372. | CH₂S(O)₂R³ | 4-N-piperdino-S(O)₂-phenyl |
| 373. | CH₂S(O)₂R³ | 4-N-pyrrolidino-S(O)₂-phenyl |
| 374. | CH₂S(O)₂R³ | Phen-2-yl |
| 375. | CH₂S(O)₂R³ | 5-NO₂-benzothiazol-2-yl |
| 376. | CH₂S(O)₂R³ | 5-NH₂-benzothiazol-2-yl |

TABLE 3-continued

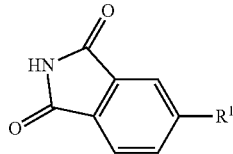

| Ex. # | R | R³ |
|---|---|---|
| 377. | CH₂S(O)₂R³ | 5-Cl-benzothiazol-2-yl |
| 378. | CH₂S(O)₂R³ | 5-cyano-benzothiazol-2-yl |
| 379. | CH₂S(O)₂R³ | 5-CH₃-benzothiazol-2-yl |
| 380. | CH₂S(O)₂R³ | 5-CF₃-benzothiazol-2-yl |
| 381. | CH₂S(O)₂R³ | 5-CH₃O-benzothiazol-2-yl |
| 382. | CH₂S(O)₂R³ | 5-CH₃C(O)-benzothiazol-2-yl |
| 383. | CH₂S(O)₂R³ | 5-CH₃OC(O)-benzothiazol-2-yl |
| 384. | CH₂S(O)₂R³ | 5-CH₃OS(O)₂-benzothiazol-2-yl |
| 385. | CH₂S(O)₂R³ | 5-H₂NC(O)-benzothiazol-2-yl |
| 386. | CH₂S(O)₂R³ | 5-H₂NS(O)₂-benzothiazol-2-yl |
| 387. | CH₂S(O)₂R³ | 5-N-piperdino-C(O)-benzothiazol-2-yl |
| 388. | CH₂S(O)₂R³ | 5-N-pyrrolidino-C(O)-benzothiazol-2-yl |
| 389. | CH₂S(O)₂R³ | 5-N-piperdino-S(O)₂-benzothiazol-2-yl |
| 390. | CH₂S(O)₂R³ | 5-N-pyrrolidino-S(O)₂-benzothiazol-2-yl |
| 391. | CH₂S(O)₂R³ | Benzothiazol-2-yl |
| 392. | CH₂S(O)₂R³ | 5-NO₂-benzimidazol-2-yl |
| 393. | CH₂S(O)₂R³ | 5-NH₂-benzimidazol-2-yl |

TABLE 3-continued

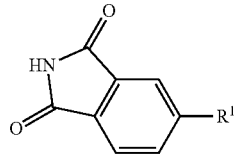

| Ex. # | R | R³ |
|---|---|---|
| 394. | CH₂S(O)₂R³ | 5-Cl-benzimidazol-2-yl |
| 395. | CH₂S(O)₂R³ | 5-cyano-benzimidazol-2-yl |
| 396. | CH₂S(O)₂R³ | 5-CH₃-benzimidazol-2-yl |
| 397. | CH₂S(O)₂R³ | 5-CF₃-benzimidazol-2-yl |
| 398. | CH₂S(O)₂R³ | 5-CH₃O-benzimidazol-2-yl |
| 399. | CH₂S(O)₂R³ | 5-CH₃C(O)-benzimidazol-2-yl |
| 400. | CH₂S(O)₂R³ | 5-CH₃OC(O)-benzimidazol-2-yl |
| 401. | CH₂S(O)₂R³ | 5-CH₃OS(O)₂-benzimidazol-2-yl |
| 402. | CH₂S(O)₂R³ | 5-H₂NC(O)-benzimidazol-2-yl |
| 403. | CH₂S(O)₂R³ | 5-H₂NS(O)₂-benzimidazol-2-yl |
| 404. | CH₂S(O)₂R³ | 5-N-piperdino-C(O)-benzimidazol-2-yl |
| 405. | CH₂S(O)₂R³ | 5-N-pyrrolidino-C(O)-benzimidazol-2-yl |
| 406. | CH₂S(O)₂R³ | 5-N-piperdino-S(O)₂-benzimidazol-2-yl |
| 407. | CH₂S(O)₂R³ | 5-N-pyrrolidino-S(O)₂-benzimidazol-2-yl |
| 408. | CH₂S(O)₂R³ | Benzimidazol-2-yl |

TABLE 4

| Ex. # | Structure |
|---|---|
| 1. | 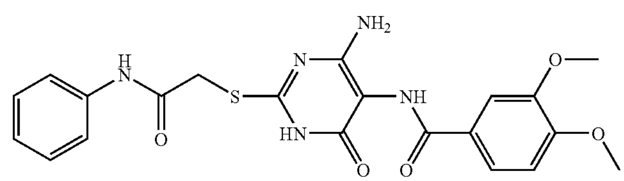 |
| 2. | 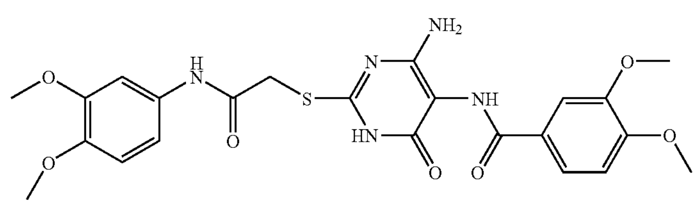 |
| 3. | 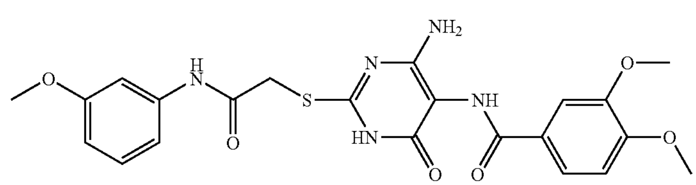 |
| 4. | 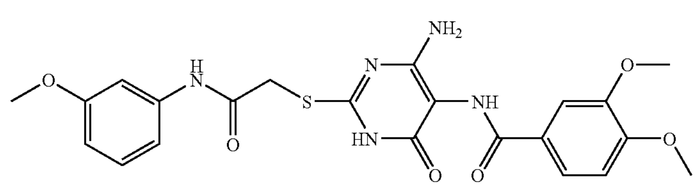 |

TABLE 4-continued

| Ex. # | Structure |
|---|---|
| 5. | (3,4-dimethylphenyl)-NHC(O)CH2-S-[4-amino-6-oxo-1H-pyrimidin-5-yl]-NH-C(O)-(3,4-dimethoxyphenyl) |
| 6. | (3-methylphenyl)-NHC(O)CH2-S-[4-amino-6-oxo-1H-pyrimidin-5-yl]-NH-C(O)-(3,4-dimethoxyphenyl) |
| 7. | (4-methylphenyl)-NHC(O)CH2-S-[4-amino-6-oxo-1H-pyrimidin-5-yl]-NH-C(O)-(3,4-dimethoxyphenyl) |
| 8. | (3-chlorophenyl)-NHC(O)CH2-S-[4-amino-6-oxo-1H-pyrimidin-5-yl]-NH-C(O)-(3,4-dimethoxyphenyl) |
| 9. | (4-chlorophenyl)-NHC(O)CH2-S-[4-amino-6-oxo-1H-pyrimidin-5-yl]-NH-C(O)-(3,4-dimethoxyphenyl) |

TABLE 5

| Ex. # | Structure |
|---|---|
| 1. | (isoxazol-3-yl)-NHC(O)CH2-S-[4-amino-6-oxo-1H-pyrimidin-5-yl]-NH-C(O)-(3,4-dimethoxyphenyl) |
| 2. | (5-chloroisoxazol-3-yl)-NHC(O)CH2-S-[4-amino-6-oxo-1H-pyrimidin-5-yl]-NH-C(O)-(3,4-dimethoxyphenyl) |

TABLE 5-continued
| Ex. # | Structure |
|---|---|
| 3. | 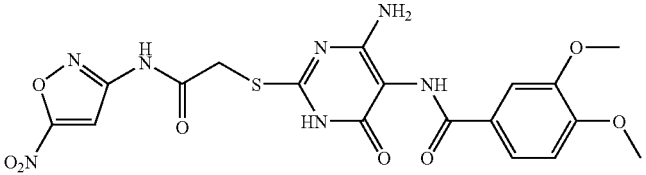 |
| 4. | 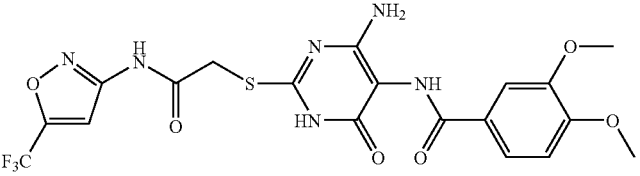 |
| 5. | 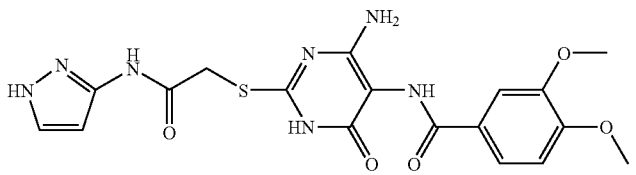 |
| 6. | 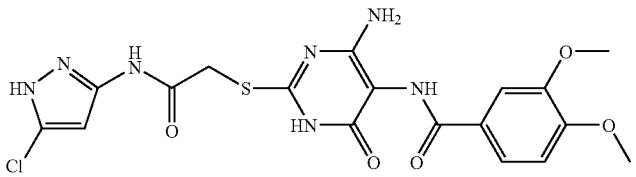 |
| 7. | 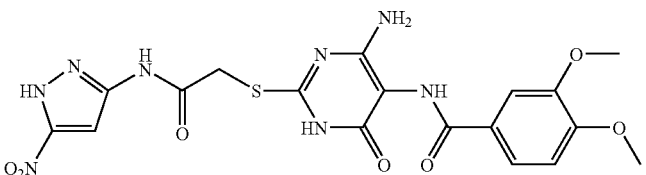 |
| 8. | 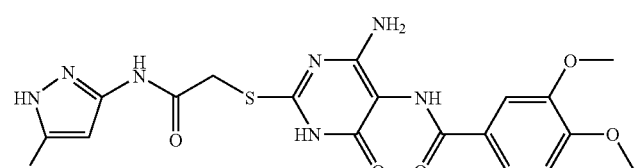 |
| 9. | 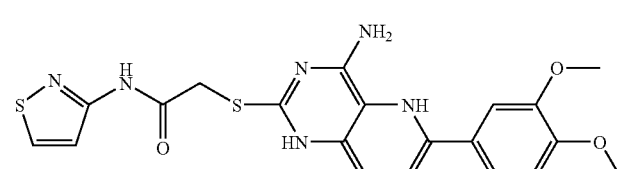 |
| 10. | 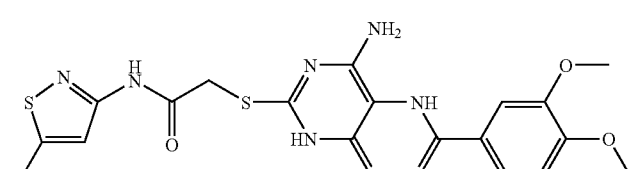 |

TABLE 5-continued
| Ex. # | Structure |
|---|---|
| 11. | ![structure 11] |
| 12. | ![structure 12] |
What is claimed is:
1. A method of inhibiting and/or causing regression of a cancerous solid breast tumor in a patient, said method comprising administering to said patient a therapeutically effective amount of a compound of formula:
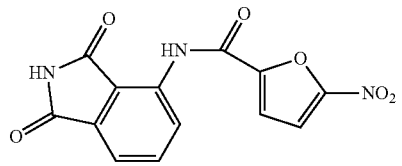
or a pharmaceutically acceptable salt thereof.
* * * * *